(12) United States Patent
Acharya et al.

(10) Patent No.: US 9,498,537 B2
(45) Date of Patent: Nov. 22, 2016

(54) METHOD OF ENHANCING EFFICACY OF BLOOD TRANSFUSIONS

(71) Applicants: Seetharama A. Acharya, Cresskill, NJ (US); Marcos Intaglietta, La Jolla, CA (US)

(72) Inventors: Seetharama A. Acharya, Cresskill, NJ (US); Marcos Intaglietta, La Jolla, CA (US)

(73) Assignees: Albert Einstein College of Medicine, Inc., Bronx, NY (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/454,059

(22) Filed: Aug. 7, 2014

(65) Prior Publication Data

US 2015/0017146 A1 Jan. 15, 2015

Related U.S. Application Data

(63) Continuation of application No. 13/794,978, filed on Mar. 12, 2013, now Pat. No. 8,859,499.

(60) Provisional application No. 61/613,105, filed on Mar. 20, 2012.

(51) Int. Cl.

| | | |
|---|---|---|
| *A61K 38/42* | (2006.01) | |
| *A61K 47/48* | (2006.01) | |
| *C07K 14/47* | (2006.01) | |
| *C07K 14/765* | (2006.01) | |
| *C07K 14/805* | (2006.01) | |
| *A61K 9/14* | (2006.01) | |
| *A61K 35/14* | (2015.01) | |
| *A61K 35/18* | (2015.01) | |
| *A61K 38/38* | (2006.01) | |

(52) U.S. Cl.
CPC .......... *A61K 47/48215* (2013.01); *A61K 9/14* (2013.01); *A61K 35/14* (2013.01); *A61K 35/18* (2013.01); *A61K 38/38* (2013.01); *A61K 38/385* (2013.01); *A61K 38/42* (2013.01); *C07K 14/47* (2013.01); *C07K 14/765* (2013.01); *C07K 14/805* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,267,269 A | 5/1981 | Grode et al. | |
| 4,356,172 A | 10/1982 | Nakao et al. | |
| 6,129,912 A | 10/2000 | Hortin et al. | |
| 6,251,927 B1 * | 6/2001 | Lai | A61K 31/11 514/365 |
| 6,384,076 B1 * | 5/2002 | Manion | A61K 38/05 514/542 |
| 6,875,423 B1 | 4/2005 | Intaglietta et al. | |
| 8,859,499 B2 * | 10/2014 | Acharya et al. | 514/15.2 |
| 2004/0259769 A1 | 12/2004 | Looker et al. | |
| 2005/0079162 A1 | 4/2005 | Page et al. | |
| 2005/0159339 A1 | 7/2005 | Acharya et al. | |
| 2005/0201988 A1 | 9/2005 | Acharya et al. | |
| 2008/0125432 A1 | 5/2008 | Blom et al. | |
| 2008/0194481 A1 | 8/2008 | Rosen et al. | |
| 2009/0298746 A1 | 12/2009 | Acharya et al. | |
| 2010/0196461 A1 | 8/2010 | Simpkins | |
| 2010/0222260 A1 | 9/2010 | Cabrales et al. | |
| 2010/0311657 A1 | 12/2010 | Abuchowski et al. | |
| 2011/0189166 A1 * | 8/2011 | Boucher | A61K 38/06 424/131.1 |
| 2012/0121720 A1 * | 5/2012 | Stamler | A61K 31/00 424/529 |
| 2013/0261061 A1 | 10/2013 | Acharya et al. | |
| 2014/0256636 A1 | 9/2014 | Acharya et al. | |

FOREIGN PATENT DOCUMENTS

| | | |
|---|---|---|
| WO | 2006135740 A1 | 12/2006 |
| WO | 2011106086 A1 | 9/2011 |
| WO | PCT/US2015/060876 | 11/2015 |

OTHER PUBLICATIONS

Ananda et al., entitled "Packign Density of the PEG-Shell in PEG-Albumins . . . Artificial," Cells, Blood Substitutes, and Biotechnology, Feb. 2012, vol. 40, pp. 14-27.

Cabrales et al., entitled "Volume resuscitation from hemorrhagic shock with albumin and hexaPEGylated human serum albumin," Resuscitation, 2008, vol. 79, pp. 139-146.

Shellington et al., entitled "Polynitroxylated pegylated hemoglobin . . . ," Critical Care Medicine, 2011, vol. 39, No. 3, pp. 494-505.

Tsai et al., entitled "Resuscitation from hemorrhagic shock . . . ," Transfusion Alternatives in Transfusion Medicine, vol. 9, pp. 246-253, (2007).

PCT International Search Report and Written Opinion, dated May 20, 2013 in connection with PCT International Application No. PCT/US2013/30355, 12 pages.

Meng F et al., entitled "Macromolecular Antioxidant Therapeutics with Pegylation-Induced Supra Perfusion: Structural and Functional Advantages of Extension Arm Chemistry for Conjugation of Antioxidant to Pegylated Proteins," Abstracts from the 2011 XIII International Symposium on Blood Substitutes and Oxygen Therapeutics [online], Jul. 2011 [retrieved on May 1, 2013] Retrieved from the Internet: <URL: http://www.medicine.mcgill.ca/artcell/536.pdf>.

(Continued)

*Primary Examiner* — Jeffrey E Russel
(74) *Attorney, Agent, or Firm* — Amster, Rothstein & Ebenstein LLP

(57) ABSTRACT

A method of improving the efficacy of a blood transfusion into a subject is provided comprising administering a composition comprising an EAF PEGylated-blood protein into the subject, prior to, during, or subsequent to the blood transfusion.

3 Claims, 7 Drawing Sheets

(56) References Cited

OTHER PUBLICATIONS

Thatte M R et al., entitled "Synthesis and Antibacterial Assessment of Water-soluble Hydrophobic Chitosan Derivatives Bearing Quaternary Ammonium Functionality." Louisana State University Ph.D Dissertation [online], Dec. 31, 2004 [retrieved on May 3, 2013]. Retrieved from the internet: <URL: http://web.archive.org/web/20041231025040/http://etd.lsu.edu/docs/available/etd-11122004-111847/>, abstract only.

Communication Supplementary European Search Report dated Mar. 22, 2016 in connection with European Patent Application No. 13764824.2, 14 pages.

Fabry M E et al., entitled "The Supra Perfusion Agent PEGylated Albumin and Its Tempol Derivative Improve Blood Oxygenation and Ameliorate Inflammatory Response in Sickle Transgenic Mice," 53rd Ash Annual Meeting and Exposition, Dec. 11, 2011, p. 2117, Abstract Only.

Cabrales P et al., entitled "Extreme hemodilution with PEG-hemoglobin vs. PEG-albumin," American Journal of Physiology: Heart and Circulatory Physiology, vol. 289, No. 6, Jan. 1, 2005. pp. H2392-H2400.

Winslow R M et al., entitled "Comparison of PEG-modified albumin and hemoglobin in extreme hemodilution in the rat," Journal of Applied Physiology, American Physiological Society, vol. 97, No. 4, Oct. 1, 2004, pp. 1527-1534.

Martini J et al., entitled "Survival time in severe hemorrhagic shock after perioperative hemodilution is longer with PEG-conjugated human serum albumin than with HES 130/0.4: a microvascular perspective," Critical Care, vol. 12, No. 2, Apr. 18, 2008, 9 pages.

Acharya S A et al., entitled "25 Engineering the Molecular Shape of PEG-Hemoglobin Adducts for Supraperfusion," Chemistry and Biochemistry of Oxygen Therapeutics: From Transfusion to Artificial Blood, Jan. 1, 2011, pp. 345-369.

Manjula B N et al., entitled "Conjugation of Multiple Copes of Polyethylene Glycol to Hemoglobin Facilitated Through Thiolation: Influence on Hemoglobin Structure and Function," Journal of Protein Chemistry, vol. 24, No. 3, Apr. 1, 2005, pp. 133-146.

* cited by examiner

METHOD OF ENHANCING EFFICACY OF BLOOD TRANSFUSIONS

CROSS-REFERENCE TO RELATED APPLICATIONS

This application is a continuation of U.S. patent application Ser. No. 13/794,978, filed Mar. 12, 2013, which claims the benefit of U.S. Provisional Patent App. No. 61/613,105, filed Mar. 20, 2012, the contents of each of which are herein incorporated by reference in their entirety.

STATEMENT OF GOVERNMENT SUPPORT

This invention was made with government support under grant numbers R24-HL 064395 and R01-HL 062354 awarded by U.S. Public Health Service (Bioengineering Research Partnership) and W81XH1120012 awarded by the US Army Medical Research and Material Command. The government has certain rights in the invention.

BACKGROUND OF THE INVENTION

Throughout this application various publications are referred to by number in parentheses. Full citations for these references may be found at the end of the specification. The disclosures of these publications and of all books, patents and patent application publications cited herein are hereby incorporated by reference in their entirety into the subject application to more fully describe the art to which the subject invention pertains.

Treatment of blood losses usually proceeds in a sequence where the initial reduction of blood volume is corrected using plasma expanders. Blood itself is used when the blood loss continues and extends beyond the so called "transfusion trigger". Outcomes in this process are significantly determined by the restoration of normal microvascular circulation—characterized by the extent to which functional capillary density (FCD) returns to normal (1). FCD is determined as the number of capillaries per unit area of tissue observed with passage of red blood cells (RBCs).

Normal FCD results from the adequate transmission of blood pressure to the periphery and the absence of capillary obstructions due to capillary collapse and abnormal blood cells. Moderate levels of colloidal plasma expansion and hemodilution up to about 50% exchange have no effects on FCD. However if bleeding follows hemodilution the conditions of the organism are significantly affected by the extent of hemodilution and volume loss, a situation described by Van der Linden and Vincent as "tolerance to hemorrhage following hemodilution," although the effect of different types of hemodiluents have not been investigated (2-4)(5).

Crystalloid and colloidal-based plasma expanders are used in the initial phase of blood volume restoration. New hypotheses are emerging on the relative efficacy of colloid based plasma expanders with significantly different biophysical properties, particularly regarding their viscosity and colloidal osmotic pressure (COP) (2-4). Clinically, human serum albumin (HSA) is also used for plasma expansion in patients (15) but hydroxyethyl starch (HES) is currently the most common clinically used colloid (5-7). Polyethylene glycol (PEG) conjugated human serum albumin (PEG-Alb) (8) has yielded improved microvascular outcomes in experimental resuscitation scenarios (9-14).

This invention provides a method of improving the efficacy of blood transfusions and of improving FCD following transfusions.

SUMMARY OF THE INVENTION

A method is provided of improving the efficacy of a blood transfusion into a subject comprising administering a composition comprising a PEGylated-blood protein into the subject, wherein the PEGylated-blood protein is administered to the subject prior to, during, or subsequent to the blood transfusion into the subject.

Also provided is a PEGylated-blood protein for improving the efficacy of a blood transfusion into a subject.

A method for treating a sickle cell disease in a subject who has received, is receiving or will receive blood transfusion to treat the sickle cell disease comprising administering to the subject a composition comprising PEGylated-blood protein or a composition comprising PEGylated-blood protein antioxidant conjugate, wherein the PEGylated-blood protein or PEGylated-blood protein antioxidant conjugate is administered to the subject prior to, during, or subsequent to the blood transfusion into the subject.

A method for reducing one or more lesions (or for reducing the extent of degradation or of oxygen-carrying capacity) resulting from, or associated with, storage of a red blood cell-containing composition, blood, or a blood derivative intended for subsequent transfusion, comprising admixing the red blood cell-containing composition, blood, or a blood derivative with an amount of EAF PEGylated-blood protein with or without an antioxidant conjugated thereto and/or of a reactive oxygen species nanomaterial in an amount effective to reduce one or more lesions (or the extent of degradation or of oxygen-carrying capacity) resulting from, or associated with, storage.

Also provided is a composition comprising (i) red blood cells, (ii) blood, or (iii) a blood derivative intended for subsequent transfusion, admixed with an amount of EAF PEGylated-blood protein with or without an antioxidant conjugated thereto and/or of a reactive oxygen species nanomaterial, as described herein, effective to reduce lesions (or for reducing the extent of degradation or of oxygen-carrying capacity) otherwise resulting from storage thereof.

Further aspects of the invention are apparent from the following description.

DETAILED DESCRIPTION OF THE INVENTION

Figure 1:
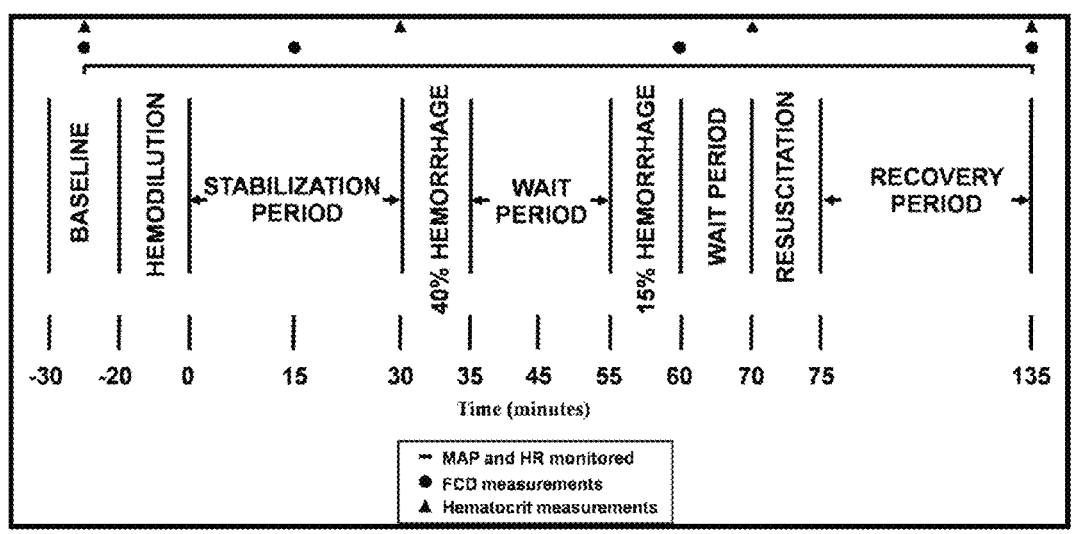
FIG. 1: The experimental protocol. Time course of the acute isovolemic exchange transfusion/hemodilution with 4% PEG-Albumin, HES, or plasma, the two-step hemorrhage procedure, and resuscitation with either fresh autologous or stored whole blood.

A method is provided of improving the efficacy of a blood transfusion into a subject comprising administering a composition comprising a PEGylated-blood protein into the subject, wherein the PEGylated-blood protein is administered to the subject prior to, during, or subsequent to the blood transfusion into the subject.

A method for treating a sickle cell disease in a subject who has received, is receiving or will receive blood transfusion to treat the sickle cell disease comprising administering to the subject a composition comprising PEGylated-blood protein or a composition comprising PEGylated-blood protein antioxidant conjugate, wherein the PEGylated-blood protein or PEGylated-blood protein antioxidant conjugate is administered to the subject prior to, during, or subsequent to the blood transfusion into the subject.

In a preferred embodiment, the composition is administered prior to the transfusion, but at less than 30 mins, less than 1 hour, less than 2 hours, less than 5 hours, less than 12 hours, or less than 24 hours before the blood transfusion into the subject. In an embodiment, the composition is administered during the transfusion. In an embodiment, the composition is administered subsequent to the transfusion, but at less than 15 mins., less than 30 mins., less than 1 hour, less than 2 hours, less than 5 hours, less than 12 hours, or less than 24 hours subsequent to the blood transfusion into the subject.

In an embodiment, the PEGylated-blood protein is an extension arm (in a conservative or a non-conservative mode) facilitated (EAF) PEGylated-blood protein. In an embodiment, the composition comprises 4% hexaPEGylated-albumin. In an embodiment, the PEG of the composition comprising the PEGylated-blood protein is 5,000 mw PEG. In an embodiment, the PEG is selected from PEG-3000, PEG-5000, PEG-7500, PEG 10,000, PEG-15,000, PEG-20,000, PEG-30,000, and/or PEG-40,000.

In an embodiment, the blood transfusion comprises blood or a blood component, and the blood or the blood component has been obtained from a blood donor more than two weeks prior to the transfusion. In an embodiment, the blood transfusion comprises blood or a blood component, and the blood or the blood component has been obtained from a blood donor more than one month prior to the transfusion.

In an embodiment, the EAF PEGylated-blood protein is oligomerized EAF PEGylated-blood protein. In an embodiment, the oligomerized EAF PEGylated-blood protein is a linear polymer. In an embodiment, the oligomerized EAF PEGylated-blood protein is a globular polymer.

In an embodiment, the blood protein is a hemoglobin. In an embodiment, the blood protein is an albumin. In an embodiment, the blood protein is hexaPEGylated.

In an embodiment, the blood protein (with or without EAF PEGylation) is covalently bonded to an antioxidant (an "EAF-PEGylated blood protein antioxidant conjugate" or a "blood protein antioxidant conjugate", respectively). In an embodiment, the blood protein is EAF polynitroxylated.

In an embodiment, the methods further comprise administering to the subject a reactive oxygen species nanomaterial as described.

In an embodiment, the methods further comprise superperfusing the EAF PEGylated-blood protein, EAF PEGylated-blood protein antioxidant conjugate and/or reactive oxygen species nanomaterial.

In an embodiment, the subject (i) has suffered a hemorrhage; (ii) is undergoing surgery; (iii) has undergone surgery within the previous 30 days; (iv) is suffering from an effect of a hemorrhagic shock; (v) has lost more than 15% of his or her blood volume within the last 48 hours; or (vi) has a sickle cell disease.

In an embodiment, the subject is in a hemodiluted state prior to the blood transfusion. In an embodiment, the composition administered comprises 1-10% EAF PEGylated-blood protein. Without being bound by theory, in an embodiment the administered compound improves functional capillary density.

In preferred embodiments of the methods described herein, the PEGylated-blood protein, the PEGylated-blood protein antioxidant conjugate, or compositions comprising such are administered into the bloodstream of the subject. In an embodiment, such can be achieved intravenously or intra-arterially. In an embodiment, such can also be achieved by administering the PEGylated-blood protein, the PEGylated-blood protein antioxidant conjugate, or compositions comprising such, as a component of the blood transfusion administered to the subject.

Also provided is a PEGylated-blood protein for improving the efficacy of a blood transfusion into a subject. In an embodiment, the PEGylated-blood protein is formulated to be administered to the subject prior to, during, or subsequent to the blood transfusion into the subject. In an embodiment, the PEGylated-blood protein is an extension arm facilitated (EAF) PEGylated-blood protein. In an embodiment, the PEGylated-blood protein or (EAF) PEGylated-blood protein has an antioxidant conjugated thereto.

As used herein, a "blood transfusion" is the administration of a quantity of whole blood, or of one or more blood products directly or indirectly into the bloodstream a subject. In non-limiting examples, blood products include one or more of red blood cells, white blood cells, plasma, clotting factors, and platelets. In an embodiment, the transfusion comprises an autologous transfusion (i.e. the transfusion blood or blood product has previously been obtained from the same subject). In a preferred embodiment, the transfusion comprises an allogeneic transfusion (i.e. the transfusion blood or blood product has been obtained from a different subject of the same species). In an embodiment, the transfusion is performed after the "transfusion trigger" has been reached in the recipient subject. Blood transfusion inefficacy can lead to various complications due in part to the need to repeat transfusions, and inefficacy can be especially serious for critical-care patients requiring rapid restoration of oxygen delivery. Insufficient efficacy can result from different causes, including blood product units damaged by storage lesion—a set of biochemical and biomechanical changes which occur during storage. With red blood cells, this can decrease viability and ability for tissue oxygenation. In an embodiment, the subject receiving, the subject who will receive or the subject who has received the blood transfusion, has not received a plasma expander. In an embodiment, the subject receiving, the subject who will receive or the subject who has received the blood transfusion, has received a plasma expander.

The "transfusion trigger" is the art-recognized critical point in the treatment subject's status at which a therapy provider, usually a physician, decides to transfuse a patient in order to achieve adequate tissue oxygenation.

Table 1 shows defined transfusion triggers (from the American Association of Critical Care Nurses):

| Source: | RBC Infusion | Platelet Infusion | FFP Infusion | Cyro Infusion |
|---|---|---|---|---|
| American Society of Anesthesiologists Guidelines for Blood Component Therapy | Rarely for Hgb >10 g/dL Usually for Hgb <6 g/dL Decision based on risk for complications related to inadequate oxygenation | Rarely for PLT >100,000 Usually for PLT <50,000 For PLT between 50,000 and 100,000 decision based on assessment of risk | Microvascular bleeding present and PT or PTT is 1.5 times normal In the absence of lab results: After transfusion of 1 total blood volume Condemns use for volume replacement | Consider for fibrinogen levels <80 mg/dL to 100 mg/dL or when levels can not be rapidly obtained |
| Coffland & Shelton | Symptoms, not Hgb and Hct, should dictate transfusion Symptomatic anemia | PLT <50,000 | Condemns use for volume replacement | Minimum therapeutic fibrinogen 50-100 mg/dL |
| Crosson | — | PLT <100,000 | Only if PT and PTT >1.5 times normal After 10 u of RBCs | Fibrinogen <150 mg/dL |
| Dennis (1992) | — | Condemns prophylactic use Bleeding times usu abnormal after 5 u RBCs; little value in determination PLT <100,000 | After 10 u of RBCs | — |
| Faringer et al (1993) | HCT <30% | Penetrating trauma with low PLT: delayed until microvascular bleeding is identified Blunt trauma with low PLT: replace promptly | Only monitor PT For PT >1.5 times normal | Fibrinogen <100 mg/dL |
| Hurley Medical Center | — | Oozing and PLT <50,000 | Initial: 2 u FFP after 10 u RBCs Followed by: 1 u FFP after each additional 5 u RBC Consider coagulation | — |
| Spence | Hgb alone should not dictate transfusion Must understand physiologic anemia | — | — | — |

Hgb = hemoglobin; Hct = hematocrit; PLT = platelets; PT = prothrombin time; PTT = partial thromboplastin time; FFP = fresh, frozen plasma; RBCs = red blood cells; Cryo = cryoprecipitate.

As used herein the "functional capillary density" (FCD) is the number of capillaries per unit volume of tissue permitting flow of RBCs.

As used herein a "blood protein" is a protein usually found in the blood of the relevant (mammalian) subject, such as hemoglobin or albumin or, if specified, a derivative thereof, such as a hemoglobin derivative showing an improved or decreased different affinity for oxygen relative to native hemoglobin. In an embodiment, the blood protein is a hemoglobin or an albumin, and includes isolated, purified or recombinant forms of each thereof. In an embodiment, the blood protein is a human hemoglobin. In an embodiment, the blood protein is a human albumin.

In embodiments, the PEG may be PEG-3000 through PEG-40,000. In an embodiment, the PEG is selected from PEG-3000, PEG-5000, PEG-7500, PEG 10,000, PEG-15,000, PEG-20,000, PEG-30,000, and/or PEG-40,000, wherein the number refers to the average molecular weight of the PEG. In an embodiment, the PEG geometry may be linear, branched, star, or comb.

In an embodiment, the blood protein is PEGylated with 1 to 100 PEG molecules, more preferably 2 to 24 PEG molecules, each attached via a flexible chemical linker (an extension arm). In a preferred embodiment, the blood protein is hexaPEGylated, with each of the PEG molecules being attached via a flexible chemical linker (an extension arm).

PEGylated blood proteins, including albumins and hemoglobins, and methods of synthesis thereof, are also described in U.S. Pat. No. 8,071,546 and in U.S. Patent Application Publication No. US 2009-0298746 A1 and in PCT International Publication No. WO 2011/106086, the contents of each of which are hereby incorporated by reference.

As used herein, an "extension arm facilitated" (EAF) PEGylated protein shall mean a protein having at least one PEG molecule attached thereto via a flexible chemical linker (an extension arm). In an embodiment where a plurality of PEG molecules are each attached via flexible chemical linkers, the extension arm facilitated PEGylated protein is capable of a lower packing density of the attached PEG chains in the PEG-shell than the packing density in the protein to which the PEG chains are linked. In an embodiment, the extension arm (i.e. the flexible small molecular weight aliphatic linker in between the protein and the PEG) is ~1 nm in length.

In an embodiment, a EAF PEGylated protein of the invention may be one of the following:

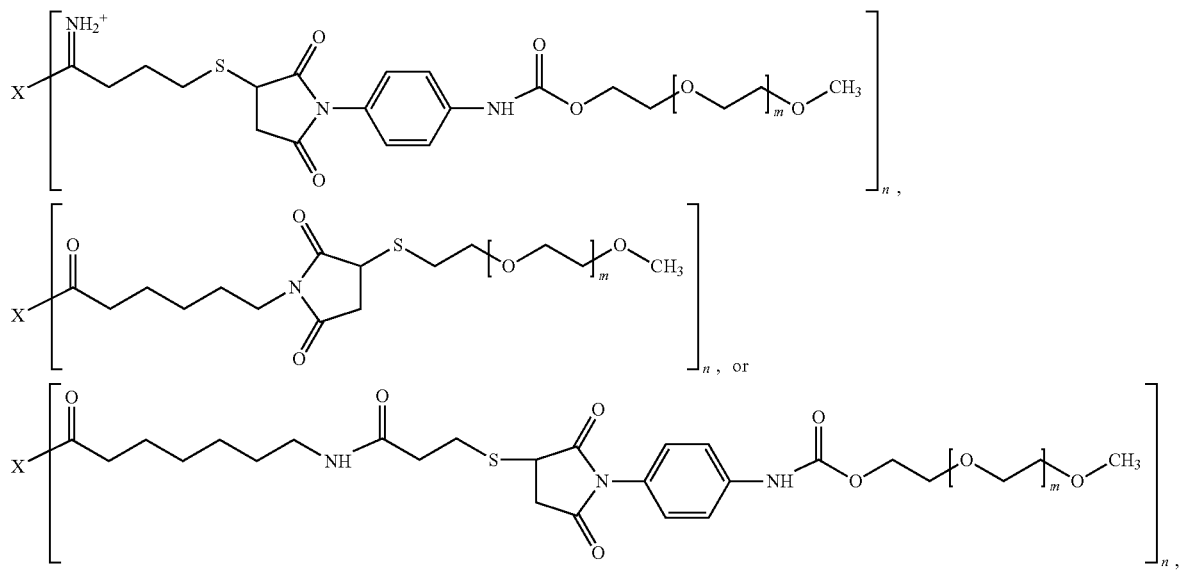

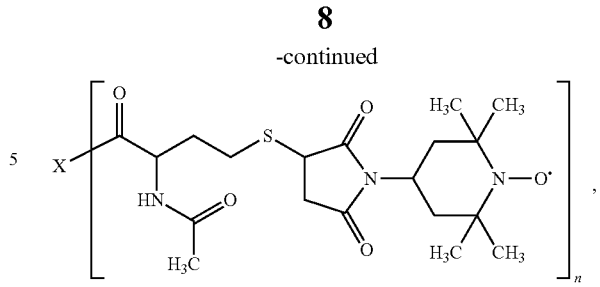

where n is an integer from 1 through 100 and X is a blood protein, such as a hemoglobin or an albumin, and wherein m is the number of ethylene glycol monomers. PEGs of from 1,000 to 40,000 daltons are preferred. The m value can be chosen to provide PEGs of from 1,000 to 40,000 daltons.

In an embodiment, the EAF PEGylated blood protein can further comprise an antioxidant. In an embodiment, the antioxidant is a thiol, thioether, glutathione, curcumin, N-acetyl methionine, or SOD mimetic (e.g., tempol (1-oxyl-2,2,6,6-tetramethyl-4-hydroxypiperidine) or a proxyl or polysulfide). In an embodiment, the EAF PEGylated blood protein can further comprise one or more of the following molecules:

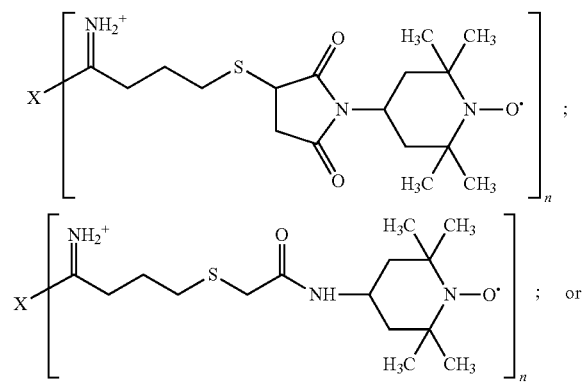

wherein X is the blood protein, (or its EAF PEGylated form, or their polymeric forms, e.g. nanomaterials), and wherein n is an integer from 1 through 100, and where the antioxidant molecule is any of the species referred to hereinabove in the tempol shown in this structure or in place of the tempol shown.

Also provided is a method for reducing one or more lesions (or for reducing the extent of degradation or of oxygen-carrying capacity) resulting from, or associated with, storage of a red blood cell-containing composition, blood, or a blood derivative intended for subsequent transfusion, comprising admixing the red blood cell-containing composition, blood, or a blood derivative with an amount of EAF PEGylated-blood protein antioxidant conjugate and/or of a reactive oxygen species nanomaterial in an amount effective to reduce one or more lesions (or the extent of degradation or of oxygen-carrying capacity) resulting from, or associated with, storage. In an embodiment, the stored red blood cell-containing composition, blood, or blood derivative is intended for subsequent transfusion to a subject. In a preferred embodiment, the subject is a human. In non-limiting examples, the red blood cell-containing composition, blood, or blood derivative is stored for one week, two weeks, three weeks, or four weeks. Also provided is a composition comprising (i) red blood cells, (ii) blood, or (iii) a blood derivative intended for subsequent transfusion, admixed with an amount of EAF PEGylated-blood protein antioxidant conjugate and/or of a reactive oxygen species nanomaterial, as described herein, effective to reduce lesions (or for reducing the extent of degradation or of oxygen-carrying capacity) otherwise resulting from storage thereof.

Also provided is a kit comprising an amount of EAF PEGylated-blood protein antioxidant conjugate and/or of a reactive oxygen species nanomaterial, as described herein, effective to reduce lesions (or for reducing the extent of degradation or of oxygen-carrying capacity) otherwise resulting from storage of (i) red blood cells, (ii) blood, or (iii) a blood derivative intended for subsequent transfusion, and instructions for use to reduce one or more of such lesions.

In an embodiment, the EAF PEGylated-blood protein antioxidant conjugate is EAF P5K6 Albumin Tempol 12 or (EAF P5K6 Albumin Tempol 12)$_n$ wherein n is a positive integer from 1 to 40. In an embodiment, the (EAF P5K6 Albumin Tempol 12)$_n$ is used and wherein n is a positive integer from 4 to 40.

Figure 5:
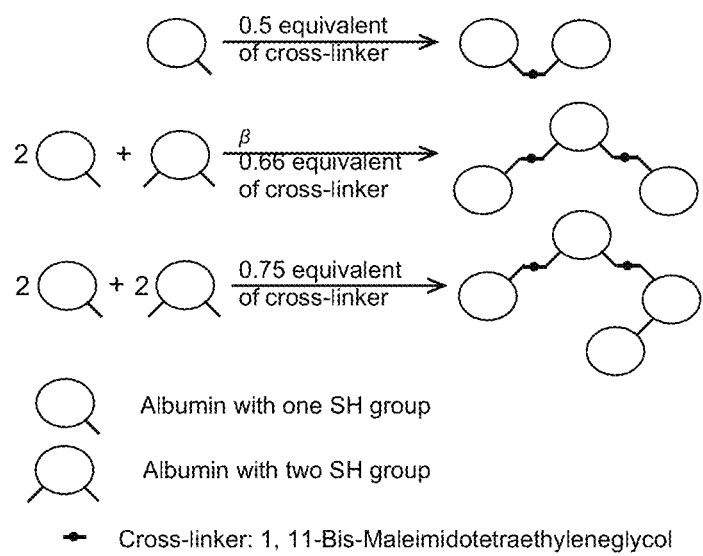
FIG. 5: Thiolation (extension arm chemistry)-mediated oligomerization of albumin using PEG bis-maleimide and limiting the intermolecular crosslink between a pair of albumin molecules to one.

Also provided is a PEGylated-blood protein oligomer having the formula (EAF P5K6 blood protein)$_n$, where n is a positive integer of from 1 to 100. In an embodiment, the PEGylated-blood protein oligomer is synthesized according to the method set forth in FIG. 5. In an embodiment of the PEGylated-blood protein oligomer, n is a positive integer of from 4 to 40.

Figure 4:
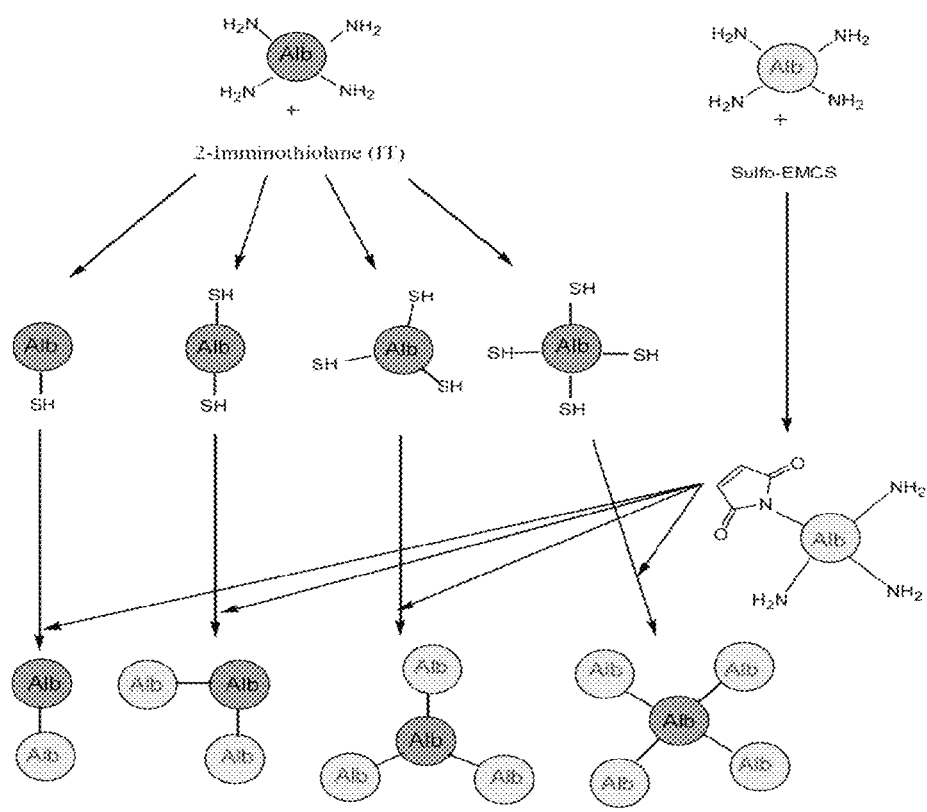
FIG. 4: Schematic representation of oligomerization of albumin by combining two different extension arm chemistry, one introducing thiol at the distal end of the extension arm (butirimidyl moiety, a conservative mode) and the other introducing maleimide moiety at the distal of the extension arm (caproylated protein, a non-conservative mode).

Also provided is a PEGylated-blood protein oligomer comprising a central blood protein with 1 to 4 further blood protein molecules attached thereto, each through an EAF linker. In an embodiment, the PEGylated-blood protein oligomer is synthesized according to the method set forth in FIG. 4.

In an embodiment of the PEGylated-blood protein oligomers, each occurrence of the blood protein is an albumin or is a hemoglobin. In an embodiment the PEGylated-blood protein oligomer comprises both albumin and hemoglobin. In an embodiment the PEGylated-blood protein oligomer further comprises one or more PEGylated-blood protein antioxidant conjugate(s) or PEGylated-blood protein SOD mimetic conjugate(s). In an embodiment, the blood protein of the PEGylated-blood protein antioxidant conjugate, is albumin.

Also provided is a PEGylated-blood protein for improving the efficacy of a blood transfusion into a subject. In an embodiment, the PEGylated-blood protein is formulated to be administered to the subject prior to, during, or subsequent to the blood transfusion into the subject. In an embodiment, the PEGylated-blood protein is an extension arm facilitated (EAF) PEGylated-blood protein. In an embodiment, the PEGylated-blood protein is further conjugated to an antioxidant. In an embodiment, each occurrence of the blood protein is an albumin or a hemoglobin.

The subject of the methods herein can be a mammal. In different embodiments, the mammal is a mouse, a rat, a cat, a dog, a horse, a sheep, a cow, a steer, a bull, livestock, a primate, or a monkey. The mammal is preferably a human.

Where a numerical range is provided herein, it is understood that all numerical subsets of that range, and all the individual integers contained therein, are provided as part of the invention. Thus, a blood protein which comprises from 1 to 100 PEG molecules includes the subset of PEGylated blood proteins which comprise 1 to 50 PEG molecules, the subset of PEGylated blood proteins which comprise 10 to 75 PEG molecules, and so forth, as well as a PEGylated blood protein which comprises 6 PEG molecules, a PEGylated blood protein which comprises 7 PEG molecules, a PEGylated blood protein which comprises 8 PEG molecules, up to and including a PEGylated blood protein which comprises 100 PEG molecules.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

The effects of PEG-Alb as an adjunct or aid to blood transfusion itself are not known. Herein, hamster plasma was used to compare PEG-albumin with albumin because plasma is approximately 70% albumin. Hamster plasma is a convenient source of hamster albumin, avoiding potential immunological effects of colloids from different species. In this context, PEGylation is proposed to render the albumin protein immune-invisible since water immobilized near the protein by PEG presumably isolates active elements from immune receptors (16). Additionally, the effects of the condition of the blood used in the transfusion process were investigated, since blood storage is known to adversely affect microvascular perfusion. Whether the outcome of resuscitation with a blood transfusion in a hemodiluted subject is dependent in any way on the colloid used prior to blood transfusion was explored, as was whether the nature of the type of colloid can overcome some of the shortcomings resulting from longer blood storage times.

The hamster chamber window model was used to compare the microvascular effects of hemodilution with fresh plasma, HES, or a 4% PEG-Alb followed by hemorrhagic shock treated by restoration of oxygen carrying capacity with fresh blood or 2-week-stored blood.

Example 2

Preparation of PEGylated blood protein, their oligomeric forms (nanomaterials) and their antioxidants: The EAF PEGylation of the blood proteins and their oligomeric forms is carried out as discussed previously (16, 19). EAF polynitroxylation of PEGylated blood proteins is also carried out just as EAF PEGylation except that maleimido phenyl urethane of PEG is replaced by tempol, and minim fast flow filtration was used to take out the excess reagents, 2-IT and maleimido Tempol.

Oligomerization of Albumin and EAF-PEGylation of the Oligomeric albumin: Oligomerization of the albumin is another desirable approach for the modulation of the solution properties, particularly viscosity of PEG-albumin. Studies by Marcos Intaglietta and Amy Tsai using alginate have exposed the correlation between the viscosity and plasma expansion, in particular vasodilation. Nonetheless, the PEG-albumin, with a significantly lower viscosity than alginate with the combination of good COP, makes it a better plasma expander than alginate. Besides dextran 70 that is isoviscous EAF P5K6 Albumin is not only vasodilatory, it also induced endothelial NO production just as dextran 500. However, it is not known how EAF P5K6 Albumin (and EAF P5K6 Hb) induces endothelial NO production, like dextran 500 does, even though the its viscosity nearly three times lower.

Generating the oligomeric forms of albumin, and EAF PEGylation, generates, for example [(EAF P5K6) Albumin] n, where n refers to number of the monomeric units in the polymer. The increased viscosity is expected to even further increase endothelial NO production. For further oligomers of albumin, two types of novel approaches for oligomerization based on the extension arm chemistry developed earlier, which chemistry is considered as a click chemistry using thiol maleimide reaction as the basic reaction. In a first approach two different extension arms are combined on two different albumin molecules, in one molecule of albumin extension arms have thiolated proteins, and in a second molecule extension arms have maleimide at the distal end. The thiolated albumin is generated by reaction the protein with 2-IT as described previously. This step of the reaction is controlled to generate Alb with one or two or three or four thiol groups on the albumin molecule. These molecular species with different levels thiols on their surface are reacted with an albumin derivative generated by reacting with one equivalent of ε-maleimido caproyl sulfo succinimide ester (sulfo EMCS). Albumin with single copy of maleimide caproyl moiety conjugated (ε-maleimido on the n chemistry (conservative and nonconservative heterobifunctional reagents to introduce intermolecular crosslinks). This is schematically presented in FIG. 4. Using iminothiolane, albumin is generated with one, two, three and four extrinsic thiols per albumin monomer. These are trapped as mixed disulfide with thiopyridyl. Since thiopyridyl groups are attached to the extrinsic thiols, the albumin molecules with different number of thiol groups will have different charges as the thiopyridyl mixed disulfides. Thus, these can be purified by conventional ion exchange chromatography.

Another class of monofunctional maleimide derivative of albumin is generated by reacting albumin with ECMS (see FIG. 4) or sulfo EMCS. Free thiols of the purified thiolated albumins are generated by releasing the mixed disulfide using TCEP (or glutathione), and mixed with maleimide-carrying albumin in amounts slightly more than one equivalent (per thiol) of the respective thiolated albumins. TCEP does not react with maleimide. The number of maleimide-carrying albumin that can be conjugated to the thiolated albumin is dictated by the number of thiols in the thiolated albumin. To quench the olgimerization reaction, low molecular weight thiol compounds are added to the reaction mixture to trap the excess maleimide-carrying albumin. Size exclusion chromatography will be used, if needed, to purify the oligomers of difined molecular size (i.e. defined number of molecules). It is expected that a pentamer can be generated by this approach. To generate oligomers with higher numbers of albumin units, a second cycle of thiolation and reaction with maleimide functionalized albumin is performed. The albumin derivative so generated has one central albumin molecule and sequentially placed layers of outer albumin. Accordingly, when it is EAF PEGylated, almost all the PEG chains conjugated thereto are surface-decorating the outer most layer of albumin molecules. These oligomers can be described as globular oligomers of EAF PEG Albumin.

In a second strategy, thiolated albumins are oligomerized using bifunctional PEG based maleimides. The principle is essentially the same as discussed above and is schematically presented below (FIG. 5). Since the design strategy introduces one crosslink between a pair of albumin molecules the resultant oligomer is an elongated molecule. Such are referred to as ellipsoidal oligomers of albumin. On EAF PEGylation, each molecule is PEGylated as there will be no steric hindrance to the access of the PEG reagent, a macromolecular reagent.

The oligomers generated by the first approach are expected to be more rigid (compact) than the oligomers generated by the second approach. Due to the flexibility of the molecule, the viscosity is expected to be higher with the later, similarly the pseudoplasticity (shear thinning effect). Very pure reagents with 4, 8, and 12 oxyethylene units are available commercially. Purified oligomers of albumin will be subjected to EAF-PEGylation to optimize the molecular, biophysical and chemical properties just as we have planned with albumin as discussed earlier.

Covalent attachment of Antioxidants (Nitroxides or thiols or methionine) to albumin and/or to PEG-albumin: For covalent attachment of nitroxides to albumin the extension arm chemistry can be used. Both conservative and non-conservative extension arm chemistry protocols are selected as desired. Conservative extension arm chemistry is preferred when larger numbers of antioxidants are to be attached to albumin. Albumin or PEG albumin is thiolated using either iminothiolane or succinimidyl esters of thiol containing aliphatic acid (commercially available). Nitroxides, TEMPOL and PROXYL are non-limiting examples of two antioxidants that can be used for generating this class of compounds. Albumin or PEG albumin is thiolated and then reacted with appropriate maleimide or iodoacetamide derivatives of the desired antioxidants. The approach is to optimize the conjugation chemistry so that the adducts generated exhibit maximum level of enzyme mimetic activity as well as longer half-life. The earlier approach has resulted in extensive electrostatic modification of the molecular surface of albumin, and this might be deemed to result in a low half-life for this product.

The enzyme mimetic activity of antioxidants of TEMPOL class (six membered ring group) is nearly two orders of magnitude higher than that of five membered series (PROXYL). Since nitroxides can recycle, the level of the antioxidant enzymem superoxide dismutase mimetic needed is expected to be very limited. The level of these compounds conjugated to albumin or PEG-albumin can be adjusted to minimize the toxicity from these antioxidants. Extension arm chemistry makes it easy to quantitate and control the level of enzyme mimetics covalently bound to albumin as well as its PEGylated product.

In addition to the nitroxide class of albumin and PEG-albumin antioxidant adducts, another class of albumin antioxidant adducts can be produced that carry extrinsic thiol functions. The extension arm chemistry used to introduce thiols for PEGylation is the approach used here. Homocysteinylation of albumin can also be used, in view of its reported high reductive potential. A third class of albumin antioxidant conjugates is albumin with multiple copies of methionine or N-acetyl methionine conjugated.

The extension arm chemistry developed introduces a thiosuccinimido moiety into molecule for each extension arm engineered. This is a thioether, and these are in principle catalase activity centers as these degrade hydrogen peroxide form reversible sulfoxides that are hydrolyzed or reduced by methionine sulfoxide reductase present in the tissues in the in vivo situations. Additional polysulfides are conjugated using the EAF bis maleimide PEG approach to increase the catalase mimetic activity, when needed, again using Extension Arm Chemistry. These classes of molecules generated from Hb and albumin are thus oxygen carrying and non-oxygen carrying plasma expanders with reactive oxygen species scavenging activity. These properties coupled with the pseudoplasticity of these, make these an unique class of reactive oxygen species scavenging activity molecules exhibiting supra perfusionary activity.

Materials and Methods

Animal preparation: Studies were performed in golden Syrian male hamsters (Charles River Laboratories, Boston, Mass.), weight range of 56-71 g. The Guide for the Care and Use of Laboratory Animals (US National Research Council, 2010) was followed for animal handling. Experiments were approved by the University of California, San Diego Institutional Animal Care and Use Committee. The window chamber model was utilized for microvascular studies in unanesthetized hamsters. Chamber implantation and vascular catheterization surgeries were performed under general anesthesia, pentobarbital 50 mg/kg or ketamine/xylazine cocktail 200/10 mg/kg i.p. injections, as previously described (17, 18). Following chamber implantation, animals recovered for a minimum two day period prior to catheterization. Animals were anesthetized for carotid artery and jugular vein catheter implantation (polyethylene-50), following microscopic chamber assessment in order to rule out edema, bleeding, or signs of infection Animals were entered into the study one to two days following catheterization surgery.

Systemic parameters: Mean arterial blood pressure (MAP) and heart rate (HR) were continuously monitored using a Biopac system (MP 150; Biopac Systems, Inc., Santa Barbara, Calif.) excluding blood sampling, hemodilution, and hemorrhage periods, where the arterial catheter was in use. Systemic hematocrit (Hct) was measured from heparinized microcapillary arterial blood collection, following centrifugation. Baseline systemic parameter requirements for inclusion of the animal in the study were: MAP>80 mmHg, HR>320 beats/min, and systemic Hct>40%.

Functional Capillary Density (FCD): FCD was determined in 10 stepwise vertically successive microscopic fields using 20× magnification. Capillaries were considered functional in having at least one transiting RBC, during a 30 sec observation period. FCD ($cm^{-1}$) can be defined as the total length of RBC-perfused capillaries divided by the surface area of tissue in which they are observed (18). Initial tissue fields were chosen by a distinguishing anatomical feature to allow quick and accurate recognition during repeated measurements.

Plasma expander fluids and experimental groups: Experiments were carried out in 3 groups of hamster (n=12 each group) each group corresponding to a plasma expander used for hemodilution (PEG-Alb, HES or plasma). Each plasma expander group was further divided into two groups (n=6 in each subdivided group) corresponding to the type of blood used in resuscitation following hemorrhage: one group received fresh autologous blood and the other group was treated with stored allogeneic whole blood. Animals were randomized into both group divisions.

Albumin PEGylation has been previously described (13, 19). An extension arm facilitated (EAF) PEGylated blood protein can be used. For example, an extension arm facilitated protocol can be used to PEGylate an albumin. In a non-limiting example, lyophilized preparations of albumin (Sigma Aldrich, St. Louis, Mo.) are subjected to cold (4° C.) EAF PEGylation for overnight at a protein concentration of 0.5 mM in the presence of 5 mM 2-IT (for thiolation of the protein) using 10 mM maleimidophenyl PEG 5 kDa (custom synthesized). Under these conditions on an average six to seven copies of PEG 5 kDa chains are conjugated to the protein. The hexaPEGylated albumin thus generated can be purified through tangential flow filtration and concentrated to a 4 gm % solution with respect to albumin (2 gm % solution with respect to PEG; it is a 6 gm % solution with respect to EAF PEG albumin calculated based on the molecular mass of EAF PEG albumin to be 95 to 100 kDa) and stored at −80° C.

The EAF PEG Albumin and EAF PEG Hb generated as described above are very distinct as compared to the products referred to Maleimide PEG modified Albumin (MPA) and Maleimide PEG modified Hb (MP) prepared by Sangart. MPA and MP4 are generated using: (a) Two-step version (protein is thiolated first and them mixed with maleimide as a second step of the reaction) of the EAF PEGylation platform and not the one-step version (thiolation and PEGylation carried out simultaneously) of EAF PEGylation discussed above; (b) Maleimido propyl PEG 5K and not Maleimido phenyl urethane of PEG 5K discussed above; (c) Baxter Albumin (a material ready to be used for transfusion), a processed human derived albumin was used for MPA, the process used involved the heating of the human derived albumin at 60° C. for 10 hrs. EAF PEG Albumin discussed here is generated using high purity human serum albumin that has not been subjected to the heating process; (d) unchromatographed human Hb (lysate) was used for the preparation of MP of Sangart, whereas Hb $A_0$ purified from the lysate by Q-Sepharose chromatography is used for the preparation of EAF PEG Hb discussed in the present study.

HES as used is a starch molecule of low molecular weight and with a low degree of molar substitution (Voluven; Fresenius-Kabi, Graz, Austria) (20).

Fresh plasma was obtained the same day of experiments from a donor hamster. Whole blood was collected in citrate and then centrifuged to obtain the plasma. The physical properties of the plasma expanders used are given in Table 2.

TABLE 2

Properties of PEG-Albumin, HES, and plasma.

| | PEG-Albumin | HES | Plasma |
|---|---|---|---|
| Source | Synthetic/Human | Synthetic | Hamster |
| Concentration (%) | 4 | 6 | — |
| Viscosity (cP) | 2.2 | 2.1 | 1.2 |
| Average molecular weight (kDa) | 96 | 130 | — |
| Suspending fluid | Phosphate buffer | Saline | — |
| Degree of substitution | — | 0.40 | — |

Collection and storage of whole blood and plasma: For fresh autologous blood collection, blood was withdrawn from the carotid artery catheter and was collected in 5 ml syringes containing citrate phosphate dextrose adenine-1 anticoagulant solution (Fenwal, Inc., Lake Zurich, Ill., CPDA-1). The amount of CPDA-1 solution used was 0.14× total blood volume (BV) withdrawn. For stored blood, blood was withdrawn from the carotid artery catheter of a donor hamster and was collected into a 5 ml syringe containing CPDA-1 (0.14× total BV=4.56 ml). The blood was then transferred under sterile conditions to a sterile preservative free vacutainer tube and immediately placed in 4° C. storage for a 14-15 day period.

Fresh plasma collection. Fresh plasma was obtained the same day as it was used from a donor hamster and collected in citrate. Donor blood was centrifuged, and plasma was separated from RBCs.

Experimental setup and acute isovolemic exchange transfusion hemorrhagic-shock and resuscitation protocol; The experimental procedure was the same for all 6 animal groups. Unanesthetized animals were placed in a restraining tube, stabilized by securing the tube and the chamber to a plexiglass stage. The plexiglass stage holding the animal was placed on an intravital microscope (BX51WI; Olympus, New Hyde Park, N.Y.) equipped with a 20× objective (LUMPFL-WIR, numerical aperture 0.5; Olympus). Animals were given 15-30 min to adjust to the tube environment before baseline measurements were taken (MAP, HR, FCD, and Hct).

Following baseline measurements, an acute anemic state was induced by a 20% of BV (estimated as 7% of individual body weight) hemodilution, through an isovolemic exchange transfusion with either 4% PEG-Albumin, HES, or fresh plasma in citrate using a dual syringe pump (model 33 syringe pump; Harvard Apparatus; Holliston, Mass.). The plasma expander was infused into the jugular vein catheter and blood was withdrawn from the carotid artery catheter at a rate of 100 μl/min. Animals were then given a 30 min stabilization period, during which FCD was measured. Systemic parameters were measured subsequent to the 30 min period, prior to the start of the two-step hemorrhage procedure. Following the stabilization period animals were subjected to a two-step hemorrhage procedure. The volume of each hemorrhage step was a calculated percentage of the animal's BV. Step one and two were 40% and 15% of BV, respectively, each carried out in a 5 min period, with a 20 min waiting period given between the first and second step of hemorrhage. Resuscitation was initiated after 10 min with a 62.7% of BV blood transfusion using either fresh autologous or stored whole blood. Resuscitation volume (62.7%) included 55% (of BV) of hemorrhaged whole blood, the balance being anticoagulant.

Fresh autologous blood was maintained at room temperature until resuscitation. Stored blood was removed from storage and allowed to warm to room temperature 30 min prior to resuscitation. Results were evaluated at 60 min after transfusion at which time the experiment was terminated. FCD and systemic parameters were assessed as shown in the experimental time table (FIG. 1).

Statistical analysis: Results are presented as mean±standard deviation, unless otherwise noted. Data are presented as absolute values and/or as values relative to baseline values. All measurements were compared with baseline levels obtained prior to the start of experimental procedures. The same capillary fields were followed in order to enable direct comparisons to their baseline levels, allowing for more robust statistics for small sample populations. For repeated measurements, within groups, time-related changes were assessed by ANOVA for nonparametric measurements (Kruskal-Wallis), and when appropriate post hoc analyses performed with the Dunn's multiple comparison test. Changes between group measurements were assessed using the Mann-Whitney test. All statistics were calculated with computer software (Prism 4.0, GraphPad, San Diego, Calif.). Changes were considered statistically significant if p<0.05.

Results

Animals studied throughout the experimental procedures completed the hemodilution phase with a MAP change no greater than 10 mmHg, indicating a successful exchange transfusion.

Hematocrit: Hct for all animal groups was decreased following hemodilution as expected and then again following the two-step hemorrhage procedure, with significant decreases resulting in all groups compared to both baseline and hemodilution values (Table 2). Hcts were restored to post-hemodilution levels, not being significantly different, after the 60 min recovery period with no significant differences between groups resuscitated with fresh autologous blood. Animals resuscitated using stored blood increased Hct following resuscitation, returning to post-hemodilution values, however, remaining significantly decreased compared to baseline levels. Transfusion of stored blood caused a significant increase in Hct 60 min post infusion for all plasma expander pre-treatments (p<0.05, Table 3).

TABLE 3

Changes in hematocrit due to hemodilution, hemorrhage, and resuscitation.

| Plasma Expander | Resuscitation Blood | Post Hemodilution | Post 15% Hemodilution | 60 min Post Resuscitation |
|---|---|---|---|---|
| PEG-Alb | Fresh autologous (n = 6) | 38.2 ± 5.7 | 22.9 ± 1.5* | 33.8 ± 2.3* |
| | Stored (n = 6) | 36.7 ± 2.4* | 25.0 ± 0.5* | 38.2 ± 2.3*[a] |
| HES | Fresh autologous (n = 6) | 40.0 ± 2.9* | 26.7 ± 1.4*[a] | 35.5 ± 2.4* |
| | Stored (n = 6) | 40.9 ± 1.5* | 27.5 ± 1.5* | 41.8 ± 1.6*[b] |
| Plasma | Fresh autologous (n = 6) | 37.8 ± 1.1* | 25.5 ± 0.8* | 34.8 ± 1.2* |
| | Stored (n = 6) | 38.5 ± 1.0* | 24.2 ± 2.2*[c] | 40.3 ± 4.6*[cd] |

Baseline hematocrit (n = 36): 48.0 ± 2.2%. Analysis within treatment groups: $p < 0.05$
*vs. baseline. Analysis between treatments at the same time point: $p < 0.05$
[a]vs. PEG-Alb Fresh blood;
[b]vs. HES Fresh blood;
[c]vs. HES Stored blood;
[d]vs. Plasma Fresh blood. 4% Peg-Albumin (Peg-Alb); Hydroxyethyl starch (HES).

Mean arterial pressure. Hemodilution caused a non-significant reduction of MAP relative to baseline. MAP decreased significantly after hemorrhage in all groups (p<0.05, Table 4). Additionally, MAP significantly decreased following hemorrhage relative to hemodilution pressures (p<0.05), apart from animals in the HES/stored blood group. Baseline MAP levels were restored for all groups 60 min post resuscitation, the effect being greater for the group treated with stored blood (p<0.05, Table 4).

TABLE 4

Effect of hemodilution, hemorrhage and resuscitation on blood pressure.

| Plasma Expander | Resuscitation Blood | Post Hemodilution | Post 15% Hemodilution | 60 min Post Resuscitation |
|---|---|---|---|---|
| PEG-Alb | Fresh, autologous (n = 6) | 106.8 ± 11.2 | 40.9 ± 9.6*† | 94.4 ± 7.8 |
| | Stored (n = 6) | 104.0 ± 8.7 | 37.7 ± 3.2*† | 116.1 ± 14.2‡[a] |
| HES | Fresh autologous (n = 6) | 108.5 ± 8.8 | 40.7 ± 14.7*† | 99.4 ± 11.3 |
| | Stored (n = 6) | 105.6 ± 3.5 | 40.6 ± 10.6* | 111.1 ± 11.6‡ |
| Plasma | Fresh autologous (n = 6) | 103.1 ± 5.7 | 32.6 ± 6.9*†[a] | 95.0 ± 7.1‡ |
| | Stored (n = 6) | 108.1 ± 9.9 | 35.6 ± 7.8*† | 110.4 ± 21.6‡ |

Baseline MAP (n = 36): 112.8 ± 9.6 mmHg. Analysis within treatment groups: $p < 0.05$
*vs. baseline;
†vs. hemodilution;
‡vs. 15% H. Analysis between treatments at the same time point: $p < 0.05$
[a]vs. PEG-Alb Fresh blood. 4% Peg-Albumin (Peg-Alb). Hydroxyethyl starch (HES).

Heart rate: Hemodilution and hemorrhage decreased HR, which was returned to near normal values by blood transfusion to an extent depending on the plasma expander used during hemodilution. The 4% PEG-Alb groups had significantly diminished HRs due to hemorrhage compared to baseline (p<0.05, Table 5). The HES animal groups only showed a significant HR variation in the fresh autologous blood resuscitated group. There were no significant differences between the HRs of HES fresh autologous and stored blood resuscitated groups. Similarly, HRs of plasma hemodiluted animals resuscitated with fresh autologous blood attained a significant difference between the post recovery period and hemorrhage values, while HRs of plasma animals resuscitated with stored blood were significantly different following hemorrhage compared with baseline and hemodilution (p<0.05). Differences between plasma fresh autologous and stored blood resuscitated animal group HRs were not significant (Table 5).

Blood gases: $PO_2$ levels for both fresh and stored blood resuscitation in all animal groups were significantly increased compared to baseline levels, following hemorrhage. $PO_2$ levels remained elevated 60 min post resuscitation, compared to baseline. However, only the PEG-Albumin and HES animal group's $PO_2$ levels remained significantly increased. The plasma animal groups returned to baseline levels (Table 6).

Base excess for all animal groups was significantly decreased compared to baseline, following hemorrhage. Resuscitation with both fresh and stored blood effectively restored base excess values for all groups, with the exception of HES fresh blood, 60 min post resuscitation.

TABLE 6

Effect of hemorrhage and resuscitation on arterial $PO_2$ and base excess.

| Plasma Expander | Resuscitation Blood | Parameter | Time Point Measurement | | |
|---|---|---|---|---|---|
| | | | Hemodilution | 15% H | R60 |
| PEG-Alb | Fresh autologous (n = 6) | $PO_2$ (mmHg) | 61.6 ± 5.8 | 108.8 ± 8.1* | 75.8 ± 8.7* |
| | | Base Excess | 5.3 ± 1.6 | −5.5 ± 3.6* | 6.6 ± 1.2‡ |
| | Stored (n = 6) | $PO_2$ (mmHg) | 66.5 ± 6.5 | 113.5 ± 9.3* | 76.1 ± 10.9* |
| | | Base Excess | 4.2 ± 1.8 | −4.4 ± 2.9* | 5.2 ± 2.2‡ |
| HES | Fresh autologous (n = 6) | $PO_2$ (mmHg) | 67.0 ± 5.9 | 132.0 ± 3.2*a | 72.9 ± 8.0* |
| | | Base Excess | 4.2 ± 2.4 | −12.4 ± 5.5* | 4.6 ± 3.3 |
| | Stored (n = 6) | $PO_2$ (mmHg) | 64.9 ± 4.0 | 121.6 ± 7.2* | 80.0 ± 15.6* |
| | | Base Excess | 5.3 ± 2.0 | −9.0 ± 3.7* | 5.2 ± 2.1‡ |
| Plasma | Fresh autologous (n = 6) | $PO_2$ (mmHg) | 60.1 ± 13.4 | 125.1 ± 4.9* | 67.0 ± 10.6 |
| | | Base Excess | 6.5 ± 1.8 | −10.8 ± 2.4* | 5.9 ± 2.2‡ |
| | Stored (n = 6) | $PO_2$ (mmHg) | 64.1 ± 6.5 | 123.2 ± 13.9* | 69.2 ± 14.2 |
| | | Base Excess | 8.2 ± 1.3 | −8.0 ± 3.8* | 7.9 ± 1.4‡ |

Baseline (n = 36): $PO_2$ 56.5 ± 5.8 mmHg and Base Excess 5.8 ± 2.0. Analysis within treatment groups: $p < 0.05$
*vs. baseline;
‡vs. 15% H. Analysis between treatments at the same time point: $p < 0.05$
[a]vs. PEG-Alb Fresh blood. Hemorrhage (H) and 60 min post-resuscitation (R60).

TABLE 5

Effect of hemodilution, hemorrhage and resuscitation on heart rate.

| Plasma Expander | Resuscitation Blood | Time Point Measurement | | |
|---|---|---|---|---|
| | | Post Hemodilution | Post 15% Hemorrhage | 60 min Post Resuscitation |
| PEG-Alb | Fresh autologous (n = 6) | 483.2 ± 9.9 | 331.8 ± 54.5*† | 475.1 ± 12.3‡ |
| | Stored (n = 6) | 475.7 ± 21.2 | 302.7 ± 30.6*† | 433.6 ± 65.2‡ |
| HES | Fresh autologous (n = 6) | 485.1 ± 15.3 | 354.0 ± 39.7† | 487.0 ± 25.0‡ |
| | Stored (n = 6) | 469.5 ± 40.8 | 331.8 ± 48.9 | 457.2 ± 60.1 |
| Plasma | Fresh autologous (n = 6) | 461.4 ± 31.8 | 329.0 ± 35.5 | 459.9 ± 13.9‡ab |
| | Stored (n = 6) | 470.1 ± 23.8 | 311.4 ± 36.5*† | 457.6 ± 68.6 |

Baseline HR (n = 36): 464.8 ± 49.1 beats/min. Analysis within treatment groups: $p < 0.05$
*vs. baseline;
†vs. hemodilution;
‡vs. 15% H. Analysis between treatments at the same time point: $p < 0.05$
[a]vs. PEG-Alb Fresh blood;
[b]vs. HES Fresh Blood. 4% Peg-Albumin (Peg-Alb). Hydroxyethyl starch (HES).

Figure 2:
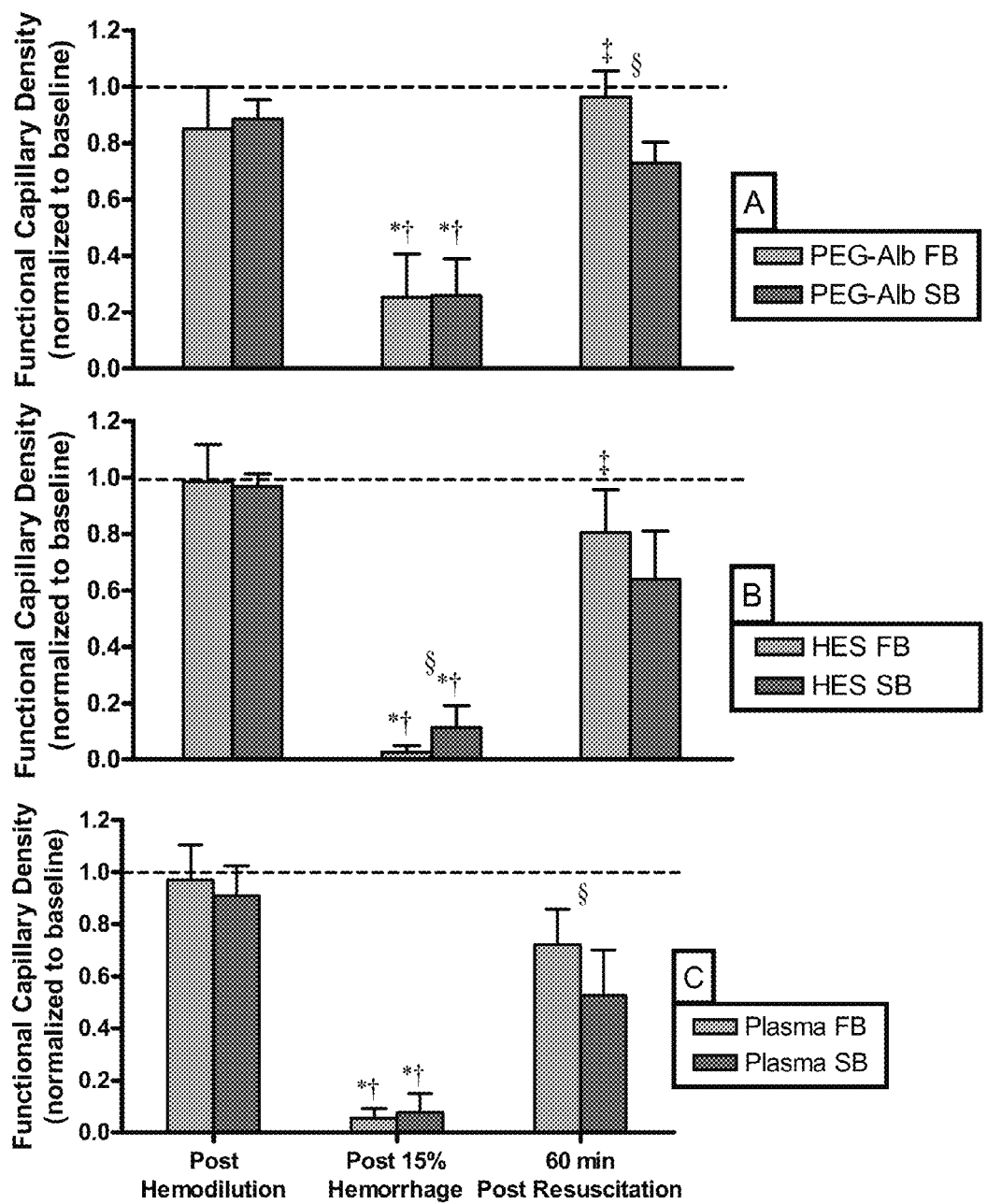
FIG. 2A-2C: Fresh autologous blood versus stored blood. Analysis within the same treatment group 4% PEG-Albumin (A), HES (B), or fresh plasma (C): P<0.05 relative to basal level (*), Hemodilution (†), 15% H (‡). Analysis between treatments at the same time point: P<0.05 (§). 4% PEG-Albumin (PEG-Alb); Fresh autologous blood (FB); Stored blood (SB).

Functional Capillary Density: There was a consistent decrease in FCD following hemodilution, hemorrhage, and 60 min post resuscitation (FIG. 2). FCD did not change in the HES/fresh autologous blood group following hemodilution. Hemorrhage significantly reduced FCD in all groups (p<0.05, FIG. 2) Animals pre-treated with HES and resuscitated with fresh autologous blood had significantly decreased FCD compared to the stored blood group (p<0.05, FIG. 2B). However, this difference was not maintained through the 60 min recovery period. Only the HES pre-treated group transfused with fresh autologous blood animals significantly increased FCD subsequent to hemorrhage (p<0.05, FIG. 2B).

Fresh autologous blood resuscitated animal groups, hemodiluted with either 4% PEG-Alb or plasma, had significantly increased FCD by comparison following resuscitation using stored blood (p<0.05, FIGS. 2A and C). However, only 4% PEG-Alb/fresh autologous blood resulted in significantly increased FCD, 60 min post resuscitation, compared to post hemorrhage values (p<0.05, FIG. 2A).

Figure 3:
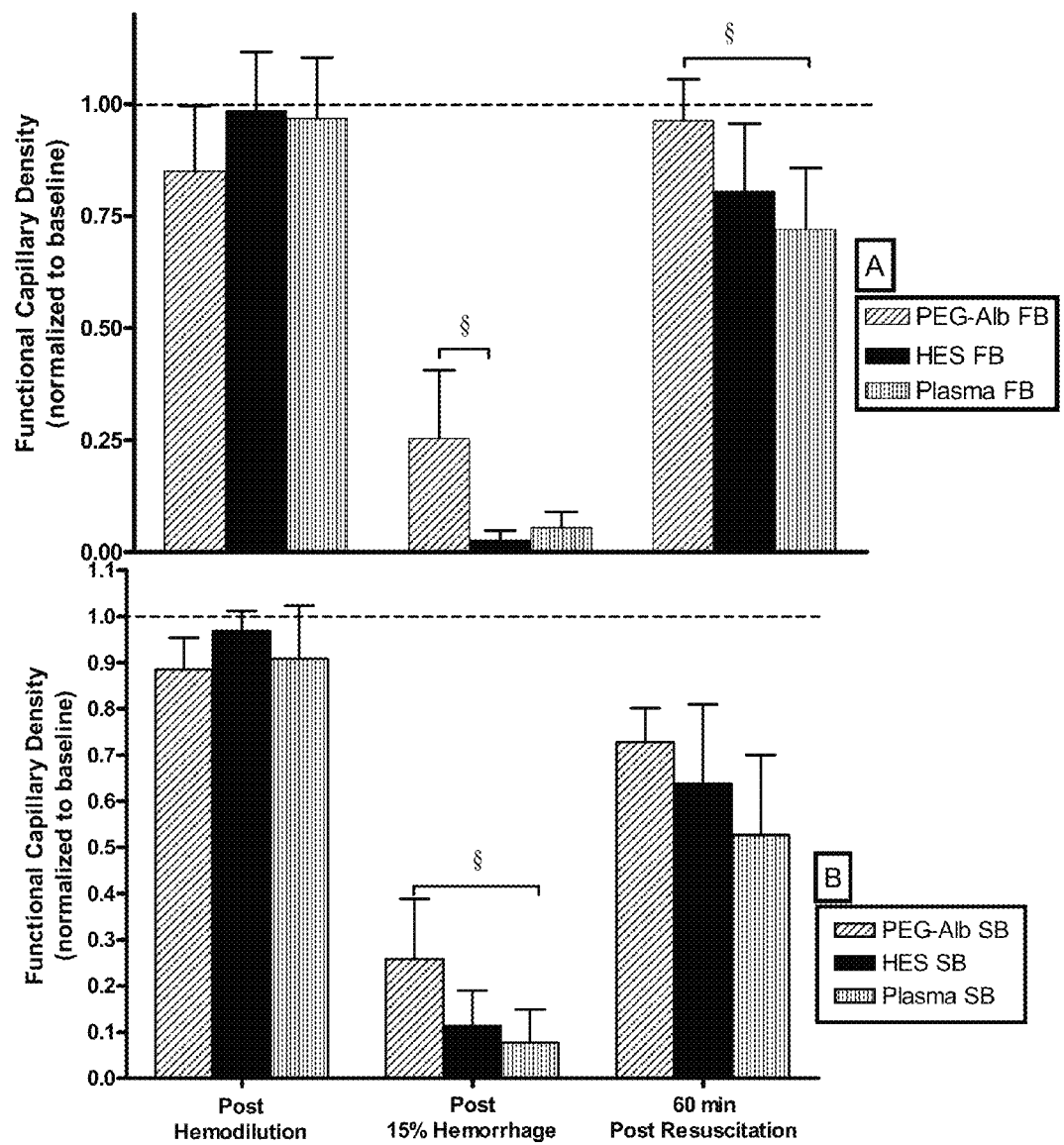
FIG. 3: Fresh autologous/stored blood: 4% Peg-Albumin vs. HES vs. plasma. Analysis between treatments at the same time point of animals resuscitated with fresh autologous (A) or stored (B) blood: P<0.05 (§). 4% Peg-Albumin (Peg-Alb); Fresh autologous blood (FB); Stored blood (SB).

FIG. 3 compares FCD for the plasma expander groups, divided according to the final use of fresh autologous or stored blood resuscitation. Four percent PEG-Alb maintained FCD during hemorrhage and produced the highest FCD 60 min after resuscitation (p<0.05, FIG. 3A).

A finding of this study is that the type of colloid used in the initial hemodilution of blood volume restitution affects the outcome FCD when blood is transfused in correcting the continuation of hemorrhage. The effect is significant, following resuscitation with fresh blood, 60 minutes after the blood transfusion, exhibiting a trend common for both fresh and stored blood whereby the best result is obtained when 4% PEG-Alb is used initially and the worst result is for fresh plasma, with HES being intermediate. The trend is statistically significant for fresh blood.

The same trend in the effect of the plasma expanders were observed for both fresh and 2-week stored blood. However, fresh blood yielded a consistently higher FCD upon transfusion by comparison to stored blood, an effect consistent with previous findings on the effects of storage on RBC properties (21). Results consistent with these were found in the study of Gonzalez et al. (22) who subjected rats to a 10% blood loss that were subsequently treated with fresh blood and 1-week and 2-weeks old stored blood. In this study the principal effect is reported to be significant 4 hr after transfusion, consisting in approximately an 8% decrease in FCD, with no difference between one and 2-week storage. This rather small effect is probably a consequence of the significantly smaller transfusion performed in their study, 10% of blood volume vs. 55% in this study.

Base excess was the same in all groups after blood transfusion. However the recovery of base excess, i.e., the change between hemorrhage (H %) and after transfusion (R60) was greater for the plasma and HES hemodilution. This in part reflects the lesser decrease of base excess with PEG-Alb hemodilution due to the better FCD during hemorrhage (FIG. 3).

The differences in systemic outcome between fresh and stored blood are evidenced by blood pressure being significantly elevated for the latter, by comparison with fresh blood. This is probably due to vasoconstriction induced by hemoglobin being liberated from RBCs during storage and from hemolysis due to increased cell fragility of the cell in the stored blood, as evidenced by the presence of plasma hemoglobin in the range of 0.1-1.7 mg/dl. Notably, differences in pre-treatment were not apparent from the measurement of MAP and HR.

The type of plasma expander used in the initial treatment of blood losses, simulated in this study by performing a 20% hemodilution, caused effects on FCD not discernible by systemic observations (MAP or HR), which were practically the same for both types of blood transfusion as shown in Tables 3 and 4. However, there were significant difference in microvascular conditions between the best (4% PEG-Alb and fresh whole blood) and worst (Fresh plasma and stored whole blood) scenarios. This interaction between blood storage times and pre-existing blood composition appear to be primarily related to how the initial plasma expansion affects microvascular function, prior to subsequent blood losses and transfusion, since the trend is already present during the shock period when the plasma expander is on board. In this context FCD is significantly higher during the shock period in animals previously hemodiluted with 4% PEG-Alb than when pre-treated with either HES or plasma.

Transfusion with fresh RBCs leads to a better outcome than using stored blood. One of the earliest investigation of this effect in conjunction with resuscitation in hemorrhagic shock was reported by Collins and Stechenberg (23), who used a model of severely stressed rats. The model consisted in exchange transfusing 90% of rat's blood volume with either fresh blood or 14-20 day stored blood at different hematocrits (17, 25, and 34%), inducing an initial state of anemia, causing hemorrhage (~50% of blood volume) and resuscitating with the same blood originally exchanged. This study showed that a difference in survival between fresh and stored blood was only evident for the anemic subjects and attributed this difference to the reduction of oxygen supply to the tissue, from the reduction in Hct and the increased oxygen affinity due to the depletion of 2, 3-DPG in the stored blood.

The present study and related results from microvascular studies suggest that the results of the Collins and Stechenberg experiment and similar studies are more specifically related to the effects on capillary flow per se rather than oxygen supply. Kerger et al. (24) showed that extended untreated hemorrhage survival correlated with the maintenance of a threshold FCD, independently of tissue oxygen, substantiating previous reports of the association between survival and improved perfusion in skeletal muscle (25). Cabrales et al. (26) reported that increased oxygen affinity in anemia improves microvascular function and Sakai et al. (27) showed that high oxygen affinity hemoglobin improves tissue oxygenation in anemia. Taken as a whole, these and other results suggest that the organism and tissue survive a considerable reduction of Hct provided that FCD is maintained. In this scenario, however, the introduction of stored RBCs has the potential of inducing negative effects because of the reduction of FCD probably due to their reduced flexibility (28) causing capillary obstruction. The associated hemolysis, liberating hemoglobin in plasma, may be an additional factor since vasoconstriction can reduce capillary pressure (29).

The clinical significance of effects found in subcutaneous/skeletal muscle tissue cannot be compared to that of internal tissues nor does its microcirculation fully represent that of internal organs such as the kidney, heart, or, viscera. However, it was found that a correlation existed between microvascular hemodynamics responses in the tissue of the window chamber and major organs (2). Thus the model is a compromise between observing microhemodynamic effects in an unexposed intact tissue, without anesthesia, and studying responses in the major organs where microhemodynamic measurements cannot be made.

PEG-Alb was originally developed previously (30), but was not extensively investigated until recently. PEG-Alb is a comparatively large molecule that immobilizes a significant amount of water on its surface. It has a relatively high COP (42 mmHg at 4% concentration), which limits its concentration in the circulation. As a consequence its potential viscogenic effect is reduced; however, its physiological effect remains similar to that of a high viscosity plasma expander, which significantly improves microvascular function in extreme anemic conditions. Four percent PEG-Alb is not particularly viscous, a property that is significantly lowered as the effective viscosity in plasma is decreased by dilution. The beneficial effects of 4% PEG-Alb appear to be due to a combination of factors, including hemodilution which reduced overall blood viscosity and increased blood flow, a modest increase in plasma viscosity, and increased nitric oxide (NO) bioavailability (31) by mechanotransduction in the endothelium.

This study focuses on events occurring at the initial stages of shock resuscitation. In previous studies it was shown that microvascular and tissue dysfunction during shock treatment with HES occurs 15 minutes after the initiation of treatment (10). In the present study it is shown that this dysfunction is only partially corrected by the restoration of oxygen carrying capacity because the critical restoration of functional capillary density is limited and dependent on blood storage. It should be noted that shock treatment is associated with a secondary decrease in microvascular flow that occurs within the first 20 to 40 min of the post resuscitation period, reported to occur in the microcirculation of the skeletal muscle, the ileum and the kidney progresses (32, 33), therefore, the observation point at 1 hour after initiation of treatment should include the effects of secondary decompensation.

In conclusion, the use of stored blood consistently yields decreased microvascular function by comparison with fresh blood, an effect reflected by many studies comparing the effects of blood storage (34). Outcome in terms of microvascular function when a blood transfusion is made following initial blood volume restoration with plasma expanders is shown to depend on the type of plasma expander, results being optimal for 4% PEG-Alb, and progressively worse for HES and homologous plasma. Thus, the microvascular outcome following a blood transfusion is dependent on how the organism and the microcirculation react to the plasma expander used prior to a blood transfusion. In addition, the microcirculation responds differentially depending on the extent of blood storage. As a corollary it appears possible to diminish the microvascular effects due to blood storage by improving pre-transfusion microvascular function.

Example 3

In further experiments, extreme hemodilution to a hematocrit (Hct) of 11% with polyethylene glycol conjugated albumin (PEG-Alb) was compared to the use of Dextran 6% 70 kDa and 6% Dextran 500 kDa in a 3 isovolemic steps protocol. Effects were analyzed by measuring the rheological properties of the plasma expander blood mixture; a model analysis of the distribution of wall shear stress in the microvessels, measurement of increased NO bioavailability above baseline levels in the vessel wall (measured using microelectrodes) and measurement of cardiac output. Plasma expansion with PEG-Alb caused a state of supraperfusion with cardiac output 40% above baseline and significantly increased NO vessel wall bioavailability and lowered peripheral vascular resistance. This condition arises because the mixture of blood and PEG-Alb is shear thinning, which as shown by a mathematical modeling of the distribution of shear stress becomes maximal at the vessel wall (wall shear stress—"WSS") and minimal in the blood vessel core. An analysis was performed using the Quemada model for describing the rheology of blood and quantifiying viscosity of blood as a function of Hct and shear rate, accounting for the presence of a cell sparse plasma layer near the vessel walls with blood plasma modeled as a Newtonian fluid. The net effect of the hemodilution using the comparatively low viscosity shear thinning PEG-Alb plasma expansion was a reduction of overall blood viscosity, an increased WSS and therefore endothelial NO production. These changes act synergistically, significantly increasing cardiac output and perfusion due to lowered overall peripheral vascular resistance.

Results for perivascular NO measurements: Six animals were entered into this study for the measurement of NO, and all animals tolerated the hemodilution protocol without visible signs of discomfort. Two animals were used as controls to insure that the system calibration and animal preparation was the same as previous control measurements (36). PEG-Alb perivascular NO levels have not been previously published. Physiological conditions and the rheological properties of blood after a level 3 exchange are presented in Table 7. For comparison, data on low viscosity hemodilution using Dextran 70, and high viscosity hemodilution using Dextran 500 from the previous study by Tsai et al. (35) is also included. The principal finding from these measurements is that the increased perfusion found in conditions of extreme hemodilution using PEG-Alb is associated with increased arteriolar and venular perivascular NO. These NO concentrations were significantly greater than in the control and when extreme hemodilution was performed Dextran 70. The NO concentrations were the same as those found using Dextran 500.

TABLE 7

Hemodilution with low viscosity Dextran 70, high viscosity Dextran 500 and PEG-Alb.

|  | Control | Dextran 70 | Dextran 500 | PEG-Alb |
|---|---|---|---|---|
| Hct, % | 49.3 ± 1.8 | 11.1 ± 0.9 | 11.0 ± 0.6 | 11.2 ± 0.7 |
| MAP, mmHg | 103 ± 6 | 64 ± 8 | 87 ± 6 | 79 ± 7 |
| Heart rate, bpm | 414 ± 35 | 418 ± 41 | 453 ± 38 | 460 ± 31 |
| Cardiac output, ml/min | 17.8 ± 1.6 | 14.2 ± 1.9 | 19.6 ± 3.5 | 24.2 ± 1.6 |
| Base-excess, mmol/l | 3.2 ± 1.5 | −4.6 ± 2.6 | 0.8 ± 1.6 | 1.3 ± 1.4 |
| Plasma viscosity, cP (#) | 1.2 ± 0.1 | 1.4 ± 0.2 | 2.2 ± 0.2 | 1.3 ± 0.1 |
| Blood viscosity, cP (#) | 4.1 ± 0.4 | 2.1 ± 0.2 | 2.8 ± 0.2 | 1.8 ± 0.1 |
| Peripheral resistance, (§) | 5.8 | 4.5 | 4.4 | 3.3 |

(#) Viscosity measured in Brookfield cone and plate viscometer at 200 sec$^{-1}$;
(§) Ratio of mean arterial blood pressure (MAP) and cardiac output.

Molecular and solution properties of (EAF-P5K6)$_n$: Without being bound by theory, it is proposed that the unique effects of EAF P5K6 Albumin in terms of increasing efficacy of blood transfusion is presumably either related to the supra-perfusion achieved by the presence of this material in the plasma or the ability of this molecule to induce endothelial NO production that increase the bioavailability of NO in the plasma. The aspects of supraperfusion and/or bioavailability of NO are linked to the viscosity and the shear thinning behavior of PEG Albumin, and this could be enhanced by the oligomerization of EAF-P5K6-albumin. One such material has been generated, and the molecular solution properties of this material is presented in Table 8.

TABLE 8

Molecular solution of properties of Oligomerized EAF PEG Albumin

|  | Molecular Radius (nm) | Molecular Volume (nm3) | PEG Shell Volume (nm3) | PEG5K chain Number1 | PEG Shell density (dal/nm3) | COP (mmHg) | Viscosity (cP) |
|---|---|---|---|---|---|---|---|
| HSA | 4.0 | 268 | — | — | — | 13.2 | 1.1 |
| PEGylated HSA 2 | 8.1 | 2226 | 1958 | 9.0 | 23.0 | 53.2 | 2.76 |
| PEGylated HSA3 | 7.7 | 1912 | 1644 | ~6 | 18.2 | 28.3 | 1.83 |
| Oligo-HSA | 14.4 4 | 12511 | — | 0 | — | — | — |
| PEGylated Oligo-HSA | 23 | 50979 | 38468 | 7.6 | 4.9 4 | 28.5 | 3.7 |

1Determined by NMR analysis.
2. Prepared at the reaction condition HSA + 2-IT + MalPEG5K(0.5:10:10 mM) reacted in PBS at 4 C. for 4 hrs.
3Prepared at the reaction condition HSA + 2-IT + MalPEG5K(0.5:5:5 mM) reacted in PBS at 4 C. for 6 hrs.
4. Assumed the average molecular number in each oligomer is about 5.

The oligomerization of the EAF PEG Albumin into the ellipsoidal form has increased the molecular dimensions to 25 nm as compared to about 7 nm for EAF PEG Albumin with six copies of PEG 5K. The viscosity of EAF PEG Albumin as expected, and also resulted in the reduction of the colloidal oncotic pressure of the material as a result of the decrease in the number of particles in solution for given weight of PEG albumin; the colloidal oncotic pressure is a colligative property of the solution. This is also good for the application of material in the present applications because the auto-transfusion of the water from the tissues to the vascular space will be reduced.

The oligomerization process has been optimized for producing EAF P5K6 Alb oligomers with molecular radius ranging from 25 nm to 100 nm, and these should now be addressed as nanoparticles rather than molecules.

Figure 6:
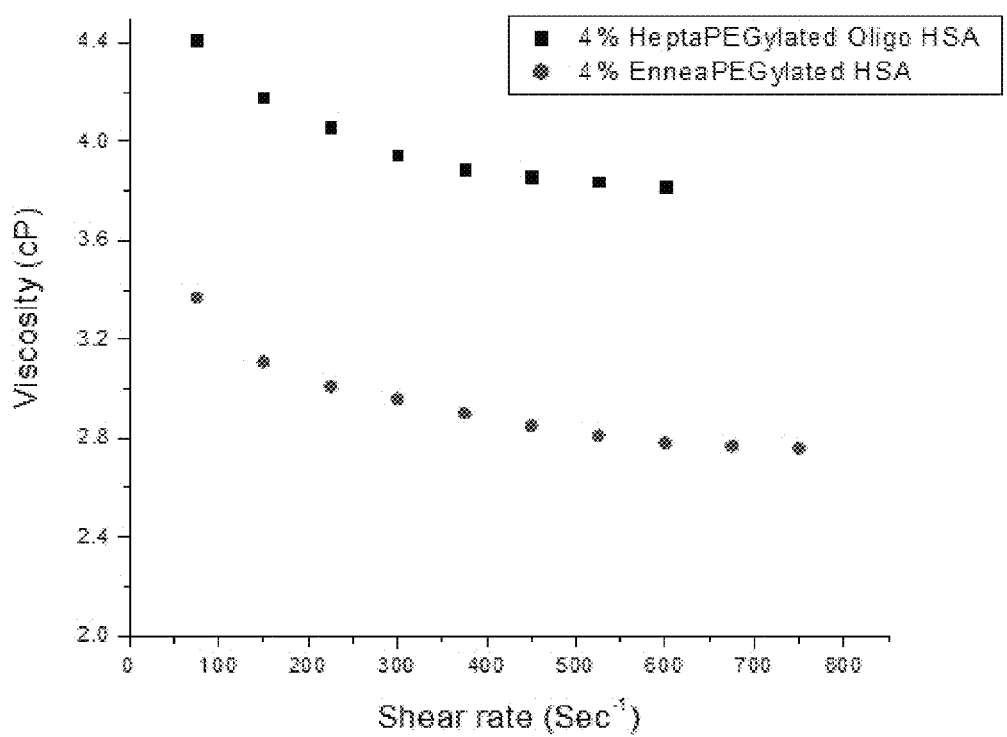
FIG. 6: Influence of EAF Bis maleimide PEG based oligomerization of EAF PEG albumin on the shear thinning effect.

Pseudoplasticity [Shear thinning effect of (EAF P5K6 Alb)$_n$]: The shear thinning effect of a 4 gm % solution of [EAF P5K6 Alb]n has been compared with that of EAF-P5K6-Alb and uncross-linked Hb in FIG. 6. Except for an increase in the viscosity of EAF PEG albumin on oligomerization, the general pattern of the shear thinning effect remains essentially unchanged.

Figure 7:
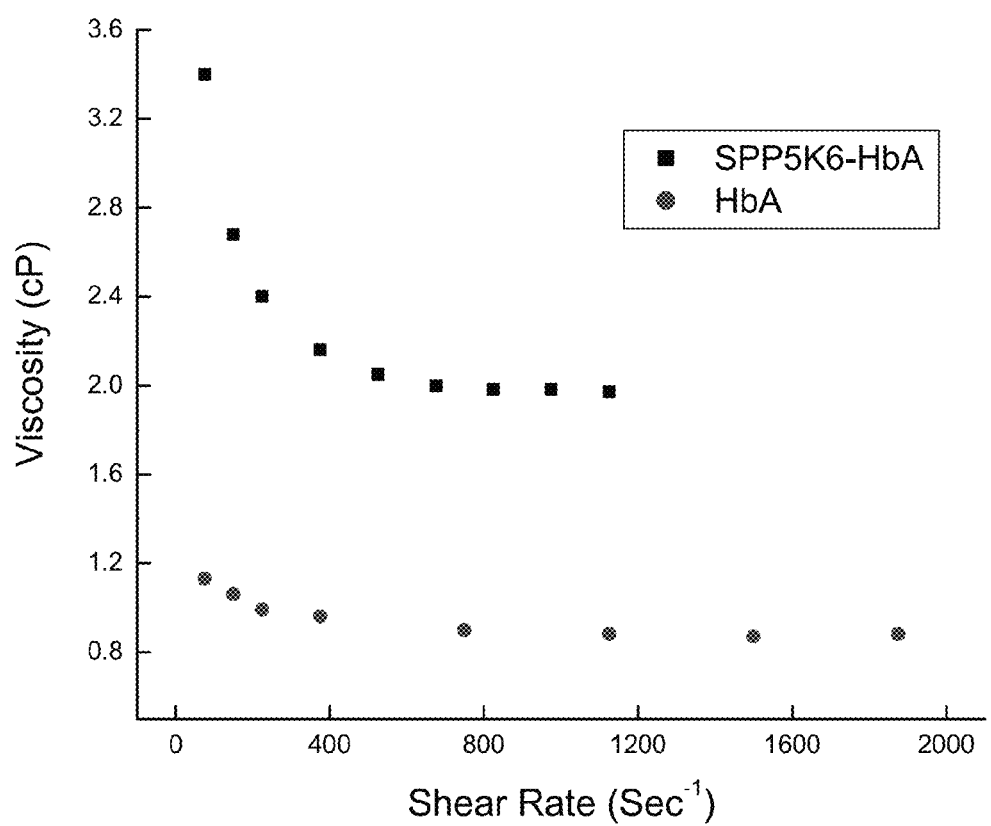
FIG. 7: Shear thinning effect of EAF PEG Hb.

The shear thinning effect of SP-P5K6-Hb: The shear thinning effect of EAF HexaPEGylated Hb has also been established and presented in FIG. 7. The shear thinning effect of EAF PEG Hb appears to be more significant than seen with EAF hexaPEGylated Albumin. The molecular dimensions of the protein core and PEG shell in EAF P5K6 Hb and EAF P5K6 Albumin are very distinct, and this appears to be responsible for this difference.

Influence of Polynitroxylation of EAF P5K6 Hb on the shear thinning effect: The polynitroxylation of EAF hexaP-EGylated Hb has also been elucidated. The polynitroxylation has been carried out using EA chemistry and the maleimido Tempol. Engineering six copies of Tempol to generate EAF P5K6 Hb-Tempol 12 has no influence on the shear thinning effect of EAF P5K6 Hb. Thus EAF PEG Albumin antioxidants and EAF PEG Hb antioxidants can be used to increase the efficacy of blood transfusion with an engineered antioxidant activity.

Comparison of the in vitro antioxidant Activity of EAF PEG Albumin Tempol 6 and EAF PEG Albumin Tempol 12: The antioxidant activity of the antioxidant activity of Tempol conjugated to albumin and Hb are compared in Table 9. The results show that conjugation of tempol to HSA by EA chemistry increases the catalytic activity of Tempol. However in the case of EAF PEG Hb, the influence of EA chemistry on the catalytic activity of tempol conjugated is much smaller, but the intrinsic activity of tempol molecule on Hb is considerably higher than that on Albumin. We consider that this may be the intrinsic peroxidase activity associated with heme centers.

TABLE 9

The O2— induced reduction rate of Hb-Tempol and HSA-Tempol nitroxides.

| | Tempo removing rate (NT/min) | (rate/min/per mole Tempol) |
|---|---|---|
| EAF P5K6-Hb-EAF-T6 | −0.278 | −0.046 |
| EAF P5K6-Hb-T1 | −0.036 | −0.036 |
| HSA-Tempo12 | −0.041 | −0.003 |
| HSA-EAF-Tempol 12 | 0.096 | 0.008 |

EA Chemistry-bis maleimiide PEG based conjugation of polysulfide to EAF PEG Alb Tempol Adducts to enhance the Efficacy of these as Reactive Oxygen Species Scavenging particles (molecules) exhibiting supra perfusionary activity: The antioxidant activity of the Tempol on EAF PEG Albumin is considerably lower than that on the EAF PEG Hb. This apparently reflects some kind of synergy between the conjugated tempol and the heme center of EAF PEG Hb. In an attempt to increase the antioxidant activity of Tempol conjugated on EAF PEG Alb, new catalase mimetic activity will be engineered by conjugation of block polymers of polypropylene sulfide. EA chemistry will be adopted for this. The polypropylene sulfide will be monofunctionally functionalized as maleimide by reacting with bis maleimide PEG (short chains 3 to 4 units of propylene oxide). The bloc polymers of propylene sulfide will be better than the thio-ether in the NEM modified thiols groups of extension arms that has been discussed. By modulating the size of the oligomer (EAF-P5K6-Albumin)n, before subjecting it to thiolation mediated polynitroxylation, and conjugation with functionalized poly propylene sulfide. The previously designed macromolecular antioxidants along with the new novel macromolecular antioxidants designed here, will serve as Reactive Oxygen Scavenging nano-materials (ROS nano-particles) with supra perfusion and will be excellent materials for antioxidant therapies and to reduce the storage lesions in RBC and to increase the efficacy of transfusion when the stored blood is used for transfusion.

Multimodal Therapy for Sickle Cell Disease (SCD): The studies have identified EAF P5K6 Albumin and EAF P5K6 Albumin Tempol 12 as the molecules (or other derivatives of this class) as antioxidant therapeutic agents for sickle cell disease. Transfusion is an accepted therapeutic approach for the treatment of the SCD. Consistent with the results presented here, the combining the two approaches for an efficient therapy for SCD is desirable.

Discussion

One significance of these findings is that they show why PEG-Alb hemodilution produces a state of supra-perfusion. This occurs because blood is diluted, lowering blood viscosity in high shear rate zones of the circulation, like the heart and major vessels; while apparent viscosity and WSS increase in the microcirculation promoting the production of NO by the endothelium and vasodilatation. An extreme case of this effect is the conversion of the fluid in the blood vessel core into a solid piston (maximum viscosity at zero shear rate), with a thin peripheral lubricating layer between the piston and cylinder. This combination of effects, which should also be operational in the heart muscle, allows the heart to maintain blood pressure and increase cardiac output, leading to the highly beneficial effect found in using PEG-Alb plasma expansion.

REFERENCES

1. Tsai A G, Cabrales P, Acharya S A, Intaglietta M: Resuscitation from hemorrhagic shock: recovery of oxygen carrying capacity or perfusion? Efficacy of new plasma expanders. *Transfusion Alternatives in Transfusion Medicine* 9:246-53, 2007.
2. Cabrales P, Tsai A G: Plasma viscosity regulates systemic and microvascular perfusion during acute extreme anemic conditions. *Am J Physiol Heart Circ Physiol* 291:H2445-52, 2006.
3. Cabrales P, Tsai A G, Ananda K, Acharya S A, Intaglietta M: Volume resuscitation from hemorrhagic shock with albumin and hexaPEGylated human serum albumin. *Resuscitation* 79:139-46, 2008.
4. Cabrales P, Tsai A G, Intaglietta M: Hyperosmotic-hyperoncotic versus hyperosmotic-hyperviscous: small volume resuscitation in hemorrhagic shock. *Shock* 22:431-7, 2004.
5. Dieterich H J: Recent developments in European colloid solutions. *J Trauma* 54:S26-30, 2003.
6. Treib J, Baron J F, Grauer M T, Strauss R G: An international view of hydroxyethyl starches. *Intensive Care Med* 25:258-68, 1999.
7. Schortgen F, Deye N, Brochard L: Preferred plasma volume expanders for critically ill patients: results of an international survey. *Intensive Care Med* 30:2222-9, 2004.
8. Winslow R M, Lohman J, Malavalli A, Vandegriff K D: Comparison of PEG-modified albumin and hemoglobin in extreme hemodilution in the rat. *J Appl Physiol* 97:1527-34, 2004.
9. Assaly R A, Azizi M, Kennedy D J, Amauro C, Zaher A, Houts F W, Habib R H, Shapiro J I, Dignam J D: Plasma expansion by polyethylene-glycol-modified albumin. *Clin Sci (Lond)* 107:263-72, 2004.
10. Cabrales P, Nacharaju P, Manjula B N, Tsai A G, Acharya S A, Intaglietta M: Early difference in tissue pH and microvascular hemodynamics in hemorrhagic shock resuscitation using polyethylene glycol-albumin- and hydroxyethyl starch-based plasma expanders. *Shock* 24:66-73, 2005.
11. Cabrales P, Tsai A G, Winslow R M, Intaglietta M: Extreme hemodilution with PEG-hemoglobin vs. PEG-albumin. *Am J Physiol Heart Circ Physiol* 289:H2392-400, 2005.
12. Hangai-Hoger N, Nacharaju P, Manjula B N, Cabrales P, Tsai A G, Acharya S A, Intaglietta M: Microvascular effects following treatment with polyethylene glycol-albumin in lipopolysaccharide-induced endotoxemia. *Crit Care Med* 34:108-17, 2006.
13. Martini J, Cabrales P, K A, Acharya S A, Intaglietta M, Tsai A G: Survival time in severe hemorrhagic shock after perioperative hemodilution is longer with PEG-conjugated human serum albumin than with HES 130/0.4: a microvascular perspective. *Crit Care* 12:R54, 2008.
14. Wettstein R, Cabrales P, Erni D, Tsai A G, Winslow R M, Intaglietta M: Resuscitation from hemorrhagic shock with MalPEG-albuming comparison with MalPEG-hemoglobin. *Shock* 22:351-7, 2004.
15. Quinlan G J, Martin G S, Evans T W: Albumin: biochemical properties and therapeutic potential. *Hepatology* 41:1211-9, 2005.
16. Veronese F M, Pasut G: PEGylation, successful approach to drug delivery. *Drug Discov Today* 10:1451-8, 2005.
17. Endrich B, Asaishi K, Gotz A, Messmer K: Technical report—a new chamber technique for microvascular studies in unanesthetized hamsters. *Res Exp Med (Berl)* 177:125-34, 1980.
18. Friesenecker B, Tsai A G, Instaglietta M: Capillary perfusion during ischemia-reperfusion in subcutaneous connective tissue and skin muscle. *Am J Physiol* 267: H2204-H12, 1994.
19. Vandegriff K D, Malavalli A, Wooldridge J, Lohman J, Winslow R M: MP4, a new nonvasoactive PEG-Hb conjugate. *Transfusion* 43:509-16, 2003.
20. Sander O, Reinhart K, Meier-Hellmann A: Equivalence of hydroxyethyl starch HES 130/0. 4 and HES 200/0. 5 for perioperative volume replacement in major gynaecological surgery. *Acta Anaesthesiol Scand* 47:1151-8, 2003.
21. Tsai A G, Hofmann A, Cabrales P, Intaglietta M: Perfusion vs. oxygen delivery in transfusion with "fresh" and "old" red blood cells: the experimental evidence. *Transfus Apher Sci* 43:69-78, 2010.
22. Gonzalez A M, Yazici I, Kusza K, Siemionow M: Effects of fresh versus banked blood transfusions on microcirculatory hemodynamics and tissue oxygenation in the rat cremaster model. *Surgery* 141:630-9, 2007.
23. Collins J A, Stechenberg L: The effects of the concentration and function of hemoglobin on the survival of rats after hemorrhage. *Surgery* 85:412-8, 1979.
24. Kerger H, Saltzman D J, Menger M D, Messmer K, Intaglietta M: Systemic and subcutaneous microvascular Po2 dissociation during 4-h hemorrhagic shock in conscious hamsters. *Am J Physiol* 270:H827-36, 1996.
25. Bond R F, Manley E S, Jr., Green H D: Cutaneous and skeletal muscle vascular responses to hemorrhage and irreversible shock. *Am J Physiol* 212:488-97, 1967.
26. Cabrales P, Sakai H, Tsai A G, Takeoka S, Tsuchida E, Intaglietta M: Oxygen transport by low and normal oxygen affinity hemoglobin vesicles in extreme hemodilution. *Am J Physiol Heart Circ Physiol* 288:H1885-92, 2005.
27. Sakai H, Tsai A G, Rohlfs R J, Hara H, Takeoka S, Tsuchida E, Intaglietta M: Microvascular responses to hemodilution with Hb vesicles as red blood cell substitutes: influence of O2 affinity. *Am J Physiol* 276:H553-62, 1999.
28. Cabrales P: Effects of erythrocyte flexibility on microvascular perfusion and oxygenation during acute anemia. *Am J Physiol* 293:H1206-15, 2007.
29. Cabrales P, Tsai A G, Intaglietta M: Microvascular pressure and functional capillary density in extreme hemodilution with low- and high-viscosity dextran and a low-viscosity Hb-based O2 carrier. *Am J Physiol Heart Circ Physiol* 287:H363-73, 2004.
30. Abuchowski A, van Es T, Palczuk N C, Davis F F: Alteration of immunological properties of bovine serum albumin by covalent attachment of polyethylene glycol. *J Biol Chem* 252:3578-81, 1977.
31. Tsai A G, Acero C, Nance P R, Cabrales P, Frangos J A, Buerk D G, Intaglietta M: Elevated plasma viscosity in extreme hemodilution increases perivascular nitric oxide concentration and microvascular perfusion. *Am J Physiol Heart Circ Physiol* 288:H1730-9, 2005.
32. Cryer H M, Gosche J, Harbrecht J, Anigian G, Garrison N: The effect of hypertonic saline resuscitation on responses to severe hemorrhagic shock by the skeletal muscle, intestinal, and renal microcirculation systems: seeing is believing. *Am J Surg* 190:305-13, 2005.
33. Peitzman A B, Billiar T R, Harbrecht B G, Kelly E, Udekwu A O, Simmons R L: Hemorrhagic shock. *Curr Probl Surg* 32:925-1002, 1995.
34. Frenzel T, Westphal-Varghese B, Westphal M: Role of storage time of red blood cells on microcirculation and tissue oxygenation in critically ill patients. *Curr Opin Anaesthesiol* 22:275-80, 2009.
35. Tsai A G, Acero C, Nance P R, Cabrales P, Frangos J A, Buerk D G, and Intaglietta M. Elevated plasma viscosity in extreme hemodilution increases perivascular nitric oxide concentration and microvascular perfusion. Am J Physiol Heart Circ Physiol 288: H1730-1739, 2005.
36. Tsai A G, Cabrales P, Manjula B N, Acharya S A, Winslow R M, and Intaglietta M. Dissociation of local nitric oxide concentration and vasoconstriction in the presence of cell-free hemoglobin oxygen carriers. Blood 108: 3603-3610, 2006.

What is claimed is:

1. A method for treating a sickle cell disease in a subject who will receive a blood transfusion to treat the sickle cell disease comprising administering to the subject a composition comprising a PEGylated-hemoglobin antioxidant conjugate prior to the blood transfusion.

2. The method of claim 1, wherein the blood transfusion comprises blood or a blood component, and the blood or the blood component has been obtained from a blood donor more than two weeks prior to the transfusion.

3. The method of claim 2, wherein the blood transfusion comprises blood or a blood component, and the blood or the blood component has been obtained from a blood donor more than one month prior to the transfusion.

* * * * *